US006297226B1

(12) United States Patent
Glasky

(10) Patent No.: US 6,297,226 B1
(45) Date of Patent: *Oct. 2, 2001

(54) SYNTHESIS AND METHODS OF USE OF 9-SUBSTITUTED GUANINE DERIVATIVES

(75) Inventor: Alvin J. Glasky, Tustin, CA (US)

(73) Assignee: NeoTherapeutics, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/419,153

(22) Filed: Oct. 15, 1999

(51) Int. Cl.[7] ..................... C07D 473/18; A61K 31/522; A61P 25/24

(52) U.S. Cl. ........................... 514/64; 514/262; 536/55.2; 544/118; 544/265; 544/230; 544/276

(58) Field of Search ..................................... 544/276, 265, 544/118, 230; 514/262, 62; 536/55.2

(56) References Cited

U.S. PATENT DOCUMENTS

| | | | |
|---|---|---|---|
| 3,300,380 | 1/1967 | Gray et al. | 167/65 |
| 4,138,562 | 2/1979 | Vince | 544/326 |
| 4,221,794 | 9/1980 | Simon et al. | 424/253 |
| 4,221,909 | 9/1980 | Simon et al. | 544/265 |
| 4,221,910 | 9/1980 | Giner-Sorolla | 544/265 |
| 4,315,920 | 2/1982 | Schaeffer et al. | 424/180 |
| 4,340,726 | 7/1982 | Simon et al. | 536/17.4 |
| 4,347,360 | 8/1982 | Ogilvie | 544/276 |
| 4,451,478 | 5/1984 | Simon et al. | 424/273 |
| 4,683,195 | 7/1987 | Mullis et al. | 435/6 |
| 4,683,202 | 7/1987 | Mullis | 435/91 |
| 5,091,432 | 2/1992 | Glasky | 514/262 |

FOREIGN PATENT DOCUMENTS

WO 91/14434
A1   10/1991   (WO) .

OTHER PUBLICATIONS

Bigge, C.F. et al, Annual Rep. Med. Chem., 29, 1994, 13–22.*
Olson, L. et al, Brain Res. Brain Res. Rev, 26, 1998, 302–5. abstract only.*
Lee, S.K. et al, J. Am. Acad. Orthop. Surg.), 8, 2000, 243–252, abstract only.*
Terenghi, G. J. Anat., 194, 1999, 1–14, abstract only.*
Lindsay, R.M., Ciba Round. Symp., 196, 39–48, abstract only.*
Tarui et al, Chem. Pharm. Bull., 44, 1996, 1998–2002.*
Fujita, Sigeo; Tanenaka, Akio; Sasada, Yoshio, Bull. Chem. Soc. Jpn., 57(7), 1707–12 (English) 1984.*
Hisatome, Masao; Maruyama, Noriaki; Ikeda, Koichi; Yamakawa, Koji, Heterocycles, 36(3), 441–4 (English) 1993.*
De Kock, D. H.; Raubenheimer, H. G., J. S. Afr. Chem. Inst., (May 24), 91–5 (English) 1971.*
Pardridge W M., Journal of Neurochemistry, (May 1998) 70 (5) 1781–92.*
Annual Reports in Medicinal Chemistry, vol. 28, James A Bristol Ed., Academic Press, San Diego, 1993, p15.*
Annual Reports in Medicinal Chemistry, vol. 30, James A Bristol Ed., Academic Press, San Diego, 1995, p 38.*
J. B. M. M. Van Bree et al, Pharm. World Sci., 15(1), 1993, 2–9.*
E. N. Conford and W. H. Oldendorf, Biochimica et Biophysica Acta, 394, 1975, 211–219.*
N.W. Tietz, ed., "Textbook of Clinical Chemistry" (W. B. Saunders Co., Philadelphia, 1986), pp. 882–886.
G.A. Lyles & B.A. Callingham, "The Effects of Thyroid Hormones on Monoamine Oxidase in the Rat Heart," *J. Pharm. Pharmacol.* 26: 921–930 (1974).
S.K. Gupta & R.K. Mishra, "Desensitization of $D_1$ Dopamine Receptors Down–Regulates the $G_s\alpha$ Subunit of G Protein in SK–N–MC Neuroblastoma Cells," *J. Mol. Neurosci.* 4: 117–123 (1993).
S.K. Gupta & R.K. Mishra, "Up–Regulation of $D_1$ Dopamine Receptors in SK–N–MC Cells After Chronic Treatment with SCH 23390," *Neurosci. Res. Commun.* 15: 157–166 (1994).
P.W. Baures et al., "Design, Synthesis, X–Ray Analysis, and Dopamine Receptor–Modulating Activity of Mimics of the 'C5' Hydrogen–Bonded Conformation in the Peptidomimetric 2–Oxo–3–(R)–[(2(S)–Pyrrolidinylcarbonyl)amino]–1–Pyrrolidineacetamide," *J. Med. Chem.* 37: 3677–3683 (1994).
J.E. Savelli et al., "Modulation of N–Methyl–D–Aspartate (NMDA) Antagonist–Induced Darting Behaviour by the Peptimimetric PAMTA," *Brain Res.* 682: 41–49 (1995).
K.A. Jacobson, "Chemical Approaches to the Definition of Adenosine Receptors" in *Adenosine Receptors* (D.M.F. Cooper & C. Londos, eds., *Receptor Biochemistry and Methodology*, J.C. Venter, L.C. Harrison, eds., Alan R. Liss: New York, 1988), pp. 11:1–26.
S.H. Appel & J.L. McManaman, "Is a Breakdown of the Blood–Brain Barrier Cause of Effect?," *Neurobiol. Aging* 7:512–514 (1986).

(List continued on next page.)

*Primary Examiner*—Mukund J. Shah
*Assistant Examiner*—Thomas C McKenzie
(74) *Attorney, Agent, or Firm*—Oppenheimer Wolff & Donnelly LLP

(57) ABSTRACT

The present invention is directed to 9-substituted guanine derivatives in which the guanine moiety is linked to another moiety with physiological or pharmacological activity through a carboxamide linkage. The number of carbon atoms between the guanine moiety and the carboxamide linking group is typically from 1 to 6. In some cases, the chemical moieties can have carbon chains of different lengths within the moiety linked to guanine through the carboxamide linker. A large number of different chemical moieties can be linked to the guanine moiety. The invention also includes pharmaceutical compositions including the 9-substituted guanine derivatives and methods of use of the 9-substituted guanine derivatives.

123 Claims, No Drawings

OTHER PUBLICATIONS

S.M. MacDonald et al., "Immunological Parameters in the Aged and in Alzheimer's Disease," *Clin. Exp. Immunol.* 49:123–128 (1982).

A.E. Miller et al., "Immunological Studies in Senile Dementia of the Alzheimer Type: Evidence for Enhanced Suppressor Cell Activity," *Ann. Neurol.* 10:506–510 (1981).

K. Stefansson, "Neuroimmunology of Aging" in *Clinical Neurology of Aging* (M.L. Albert, ed., Oxford University Press, Oxford, (1984)), ch. 4, pp. 76–94.

L.R. Weitkamp et al.,"Alzheimer Disease: Evidence for Susceptibility Loci on Chromosomes 6 and 14," *Am. J. Hum. Genet.* 35:443–53 (1983).

A. Yamazaki et al., Synthesis of Guanosine and Its Derivatives from 5–Amino–1–β–D–Ribofuranosyl–4–Imidazolecarboxamide I. Ring Closure with Benzoyl Isothiocyanate,*J. Org. Chem.* 32:1825–1828 (1967).

B. Alhede et al., "A Simple and Efficient Synthesis of 9–Substituted Guanines. Cyclodesulfurization of 1–Substituted 5–[(Thiocarbamoyl)amino]imidazole–4–carboxamides under Aqueous Basic Conditions," *J. Org. Chem.* 56:2139–2143 (1991).

R.E. Callard & A.J.H. Gearing, "The Cytokine Facts Book" (Academic Press, London, 1994), pp. 99–100, 104–105, 191–200, 235–237.

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Morradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788: 87–94 (1998).

W.M. Pardridge, "CNS Drug Design Based on Principles of Blood–Brain Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–509 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols,* (G.B. Irvine & C.H. Williams, eds., Humana Press, Totowa, NJ, 1997), pp. 353–360.

M.P. Rathbone et al., "Physiology and Pharmacology of Natural and Synthetic Nonadenine–Based Purines in the Nervous System," *Drug. Develop. Res.* 45: 356–372 (1998).

M.P. Rathbone et al., AIT–082 as a Potential Neuroprotective and Regenerative Agent in Stroke and Central Nervous System Injury, *Exp. Opin. Invest. Drugs* 8: 1255–1262 (1999).

W.A. Banks et al., "Effects of Wheatgerm Agglutinin and Aging on the Regional Brain Uptake of HIV–1 gp120," *Life Sci.* 65: 81–89 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O. Chu–LaGraff et al., "Effect of AIT–082 on Brain NGF mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

Hisatome, Masao, Maruyama, Noriaki, Ikeda, Koichi, Furutera, Tetsuo Ishikawa, Tomiyasu and Yamakawa, Koji. *Chem. Pharm. Bull* 44(10), Synthesis and Some Spectroscopic Properties of Porphyrin Derivatives Connected with Nucleobases by Alkanamide Chains, 1996, pp 1801–1811, Tokyo, Japan.

\* cited by examiner

SYNTHESIS AND METHODS OF USE OF 9-SUBSTITUTED GUANINE DERIVATIVES

FIELD OF THE INVENTION

The present invention is directed to 9-substituted guanine derivatives. More particularly, the present invention is directed to 9-substituted guanine derivatives that are bifunctional compounds in which the guanine is covalently linked to another moiety having physiological or biological activity.

BACKGROUND OF THE INVENTION

The modification of pharmaceutical and biologically active compounds to alter or enhance their functional properties is known in the art. Typically, prior art efforts have been directed to the production of carrier-bound drugs in which carrier molecules having selective physical properties, such as enhanced water solubility, are chemically attached to biologically active compounds. For example, Jacobson and colleagues have developed what is referred to as the "functional congener" approach to the design of carrier-bound drugs (K. A. Jacobson, in *Adenosine Receptors* (D. M. F. Cooper & C. Londos, eds., *Receptor Biochemistry and Methodology*, J. C. Venter, L. C. Harrison, eds., Alan R. Liss: New York, 1988), pp. 11:1–26). This approach involved a modification of well defined drug molecules at non-sensitive positions in a manner that retained the drug's ability to bind at a specific receptor site. In order to produce a chemically functionalized drug congener, they modified the drug molecule through the identification of a chemical functional group which could then be covalently attached to a carrier molecule. This produced a bifunctional molecule in which one portion (the "pharmacophore") contributed its biological activity, and the second portion, or carrier, imparted its selective physical properties such as enhanced receptor attachment or water solubility. Using this approach, functional congener compounds were prepared using catecholamines, adenosine receptor agonists and antagonists, and muscarinic agents.

However, recent developments in the understanding of biological mechanisms such as the binding of selective ligands to receptors and their related functions in seemingly diverse physiological systems as the cardiovascular system, the central nervous system, and the immune system have stimulated efforts to discover alternative methods for designing biologically active compounds exhibiting properties which will selectively treat or regulate such seemingly diverse chemical systems without serious or disabling side effects. For example, adenosine receptors have been found in the cardiovascular system, the central nervous system, and the immune system. Accordingly, it was originally believed that the development of adenosine analogues would be effective in regulating or modifying the biological activities associated therewith. However, the ubiquitous distribution of adenosine receptors has resulted in the production of serious and disabling side effects in what were originally believed to be unrelated biological systems, thereby significantly reducing the therapeutic usefulness of adenosine analogues.

Similarly interrelationships have also been discovered to exist in the mammalian immune system and the mammalian nervous system. Over the past several decades numerous researchers have added considerable detail to the overall understanding of the mammalian immune system and its importance in maintaining overall physical health. In more recent years, similar detail has evolved in the study of the nervous system. As more and more information is developed in these seemingly independent fields of study, a number of close functional parallels begin to appear between the two physiological systems. For example, both systems are concerned with the storage of information and use soluble chemicals to transmit signals between cells. Additionally, natural indigenous substances, such as hormones and transmitters, are active on the cells of both systems. Even more significantly, some common functions between the two systems are based upon similar chemical structures or markers on the surfaces of both nerve cells and immune cells. The recent discovery that the CD4 receptors targeted by the AIDS virus are present on both T4 lymphocytes and on neurons as one of the more dramatic examples of a close relationship between the nervous system and the immune system.

Further crossing the classically imposed barriers between the fields of immunology and neurology, recent developments in the understanding of Alzheimer's disease have implicated an immunological component that may be present in this neurological disorder. It has been proposed that both the anatomical and biochemical specificity of the defects seen in Alzheimer's disease could be explained by an immunological attack on the brain blood vessels themselves with secondary involvement of neuronal, glial, or synaptic constituents contributing to the formation of senile plaques, or an immune-mediated compromise of vessels associated with an immune attack on specific neuronal, glial, or synaptic constituents (S. H. Appel, *Neurobiol. Aging* 7:512 (1986)).

Additionally, circumstantial evidence for an immunological component in neurological disorders is also provided by the altered suppressor cell function in aging populations, and more specifically in Alzheimer's disease (MacDonald et al., *Clin. Exp. Immunol.* 49:123–128 (1982); A. E. Miller, *Ann. Neurol.* 10:506–510 (1981); K. Stefansson in *Clinical Neurology of Aging* (M. L. Albert, ed., Oxford University Press, Oxford, (1984), pp. 76–94), by the implication of HLA regions of chromosome 6 and GM locus of chromosome 14 in a large kindred with Alzheimer's disease (L. R. Weitkamp, *Am. J. Hum. Genet.* 35:443–53 (1983)), and by the altered immunological parameters in Down's syndrome, a disease whose symptoms are similar to senile dementia of the Alzheimer's type (SDAT).

Scientists in the nascent field of neuroimmunology have hypothesized the defects and the function of brain cells (neurons) may be observed concomitantly as parallel defects or deficiencies and receptors on the cells of the immune system (such as peripheral blood immune cells). The validity of this hypothesis was recently brought to light with the aforementioned discovery of HIV infection in neurons. This neuroimmunological theory has had significant impact because formerly almost all neuropsychiatric disorders were thought to be primarily due to factors such as genetic predisposition, mental attitudes, and/or resistance to natural environment rather than defects or deficiencies in cell function. Similarly, though the immune system has been implicated in numerous diseases ranging from infection and cancer to degenerative diseases such as Alzheimer's disease, arthritis, and aging, its relationship to cognitive functioning was previously unrealized.

Because the chemical interrelationship between these diverse physiological systems has been recognized only recently, prior art medical treatments and pharmaceutical agents have focused almost exclusively on treating the individual systems alone. Thus, pharmaceutical compounds have been developed for treating or regulating the cardiovascular system or the immune system or the central nervous system with the idea of avoiding undesirable interactions in what are now known to be related physiological systems. By far the greatest amount of recent effort in the pharmaceutical and medical fields has been devoted to the treatment and/or regulation of the immune system alone. Numerous immunomodulating and antiviral agents have been disclosed in the art such as those described in European Patent Publication No. 0126813 by Simon et al., U.S. Pat. No. 4,221,909 to Simon et al., U.S. Pat. No. 4,211,794 to Kraska, and U.S. Pat. No. 4,221,910 to Giner-Sorolla. Unlike antibiotics which directly attack or destroy invading organisms such as bacteria, immunomodulating agents and more specifically immune enhancing agents are compounds which help to bolster the body's own defense mechanism against the effects of infections. Immunomodulating agents either restore the suppressed immune function, or suppress hyperactive immune function.

Though the AIDS epidemic has focused considerable resources and attention to the study of defects and deficiencies in the immune system, outside of the recent discovery of HIV infection in neuronal tissue, comparatively little research has been directed to the development of multifunctional pharmaceutical compounds such as neuroimmunologic agents or other compounds exhibiting functionally related and mutually supportive therapeutic activities such as immunomodulating with cardiovascularly active compounds or immunomodulating with anti-microbially active compounds.

Accordingly, there is a need for compounds that are bifunctional and that can interact with multiple receptors on the surface of different cell types. There is also a particular need for compounds that pass through the blood-brain barrier so that the activities of such compounds can be exerted in the central nervous system, such as for the treatment of diseases such as Alzheimer's disease, amyotrophic lateral sclerosis (Lou Gehrig's disease), and other neurodegenerative diseases. A number of such compounds and methods for synthesizing them are disclosed in U.S. Pat. No. 5,091,432 to Glasky, incorporated herein by this reference. This includes a number of bifunctional compounds that pass through the blood-brain barrier, particularly 4-carboxyphenyl-3-(6-oxohydropurin-9-yl) propanamide.

There is particular interest in the development of bifunctional compounds in which one of the active moieties is a guanine analogue. Guanine analogues are involved in the regulation of a number of biochemical reactions in nervous tissue. In particular, guanine analogues mediate the activation of adenylate cyclase by the $G_s$ protein. In addition, there are other proteins involved in regulation in the central nervous system that bind guanine analogues, such as the $G_o$ protein. Therefore, there is a particular need for such bifunctional compounds in which one of the moieties is guanine or a guanine analogue.

SUMMARY

The present invention is directed to 9-substituted guanine derivatives of formula (I) through (XLIX) wherein n, the number of carbon atoms between the guanine moiety and the carboxamide linking group, is from 1 to 6. The 9-substituted guanine derivatives have a number of different chemical moieties linked to the guanine moiety through the carboxamide linker. In some cases, the chemical moieties can have carbon chains of different lengths within the moiety linked to guanine through the carboxamide linker.

In particular, the invention includes the following:

(1) a 9-substituted guanine derivative of formula (I) wherein n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH;

(2) a 9-substituted guanine derivative of formula (II) wherein n is an integer from 1 to 6;

(3) a 9-substituted guanine derivative of formula (III) wherein n is an integer from 1 to 6;

(4) a 9-substituted guanine derivative of formula (IV) wherein n is an integer from 1 to 6, p is an integer from 1 to 6, and q is an integer from 1 to 3;

(5) a 9-substituted guanine derivative of formula (V) wherein n is an integer from 1 to 6, $R_1$ is selected from the group consisting of H, COOH, and $COOW_1$, where $W_1$ is selected from the group consisting of lower alkyl, amino, and lower alkylamino, $R_2$ is selected from the group consisting of H and OH, and $R_3$ is selected from the group consisting of H and OH;

(6) a 9-substituted guanine derivative of formula (VI) wherein n is an integer from 1 to 6 and p is an integer from 1 to 3;

(7) a 9-substituted guanine derivative of formula (VII) wherein n is an integer from 1 to 6 and p is an integer from 1 to 3;

(8) a 9-substituted guanine derivative of formula (VIII) wherein n is an integer from 1 to 6 and p is an integer from 1 to 6;

(9) a 9-substituted guanine derivative of formula (IX) wherein n is an integer from 1 to 6;

(10) a 9-substituted guanine derivative of formula (X) wherein n is an integer from 1 to 6 and p is an integer from 1 to 6;

(11) a 9-substituted guanine derivative of formula (XI) wherein n is an integer from 1 to 6 and p is an integer from 1 to 3;

(12) a 9-substituted guanine derivative of formula (XII) wherein n is an integer from 1 to 6 and p is an integer from 1 to 6;

(13) a 9-substituted guanine derivative of formula (XIII) wherein n is an integer from 1 to 6 and p is an integer from 1 to 6;

(14) a 9-substituted guanine derivative of formula (XIV) wherein n is an integer from 1 to 6 and p is an integer from 1 to 6;

(15) a 9-substituted guanine derivative of formula (XV) wherein n is an integer from 1 to 6;

(16) a 9-substituted guanine derivative of formula (XVI) wherein n is an integer from 1 to 6;

(17) a 9-substituted guanine derivative of formula (XVII) wherein n is an integer from 1 to 6;

(18) 9-substituted guanine derivative of formula (XVIII) wherein n is an integer from 1 to 6 and p is an integer from 1 to 6;

(19) a 9-substituted guanine derivative of formula (XIX) wherein n is an integer from 1 to 6;

(20) a 9-substituted guanine derivative of formula (XX) wherein n is an integer from 1 to 6 and p is an integer from 1 to 6;

(21) a 9-substituted guanine derivative of formula (XXI) wherein n is an integer from 1 to 6;

(22) a 9-substituted guanine derivative of formula (XXII) wherein n is an integer from 1 to 6 and p is an integer from 1 to 6;
(23) a 9-substituted guanine derivative of formula (XXIII) wherein n is an integer from 1 to 6;
(24) a 9-substituted guanine derivative of formula (XXIV) wherein n is an integer from 1 to 6 and p is an integer from 1 to 3;
(25) a 9-substituted guanine derivative of formula (XXV) wherein n is an integer from 1 to 6;
(26) a 9-substituted guanine derivative of formula (XXVI) wherein n is an integer from 1 to 6 and p is an integer from 1 to 3;
(27) a 9-substituted guanine derivative of formula (XXVII) wherein n is an integer from 1 to 6 and p is an integer from 2 to 6;
(28) a 9-substituted guanine derivative of formula (XXVIII) wherein n is an integer from 1 to 6, p is an integer from 1 to 6, and q is an integer from 1 to 3;
(29) a 9-substituted guanine derivative of formula (XXIX) wherein n is an integer from 1 to 6;
(30) a 9-substituted guanine derivative of formula (XXX) wherein n is an integer from 1 to 6 and p is an integer from 1 to 6;
(31) a 9-substituted guanine derivative of formula (XXXI) wherein n is an integer from 1 to 6 and p is an integer from 1 to 6;
(32) a 9-substituted guanine derivative of formula (XXXII) wherein n is an integer from 1 to 6 and p is an integer from 1 to 6;
(33) a 9-substituted guanine derivative of formula (XXXIII) wherein n is an integer from 1 to 6 and p is an integer from 2 to 6;
(34) a 9-substituted guanine derivative of formula (XXXIV) wherein n is an integer from 1 to 6 and p is an integer from 1 to 6;
(35) a 9-substituted guanine derivative of formula (XXXV) wherein n is an integer from 1 to 6 and R is a lower alkyl residue of $C_1$ to $C_6$;
(36) a 9-substituted guanine derivative of formula (XXXVI) wherein n is an integer from 1 to 6 and R is a lower alkyl residue of $C_1$ to $C_6$;
(37) a 9-substituted guanine derivative of formula (XXXVII) wherein n is an integer from 1 to 6;
(38) a 9-substituted guanine derivative of formula (XXXVIII) wherein n is an integer from 1 to 6;
(39) a 9-substituted guanine derivative of formula (XXXIX) wherein n is an integer from 1 to 6 and p is an integer from 1 to 6;
(40) a 9-substituted guanine derivative of formula (XL) wherein n is an integer from 1 to 6, p is an integer from 2 to 6, and R is a lower alkyl residue of $C_1$ to $C_6$;
(41) a 9-substituted guanine derivative of formula (XLI) wherein n is an integer from 1 to 6 and p is an integer from 1 to 3;
(42) a 9-substituted guanine derivative of formula (XLII) wherein n is an integer from 1 to 6 and p is an integer from 1 to 6;
(43) a 9-substituted guanine derivative of formula (XLIII) wherein n is an integer from 1 to 6;
(44) a 9-substituted guanine derivative of formula (XLIV) wherein n is an integer from 1 to 6;
(45) a 9-substituted guanine derivative of formula (XLV) wherein n is an integer from 1 to 6;
(46) a 9-substituted guanine derivative of formula (XLVI) wherein n is an integer from 1 to 6;
(47) a 9-substituted guanine derivative of formula (XLVII) wherein n is an integer from 1 to 6;
(48) a 9-substituted guanine derivative of formula (XLVIII) wherein n is an integer from 1 to 6 and R is a lower alkyl residue of $C_1$ to $C_6$; and
(49) a 9-substituted guanine derivative of formula (XLIX) wherein n is an integer from 1 to 6.

Formulas (I)–(XLIX) are given below.

Another aspect of the invention is pharmaceutical compositions comprising:

(1) an effective amount of a 9-substituted guanine derivative according to the present invention; and (2) a pharmaceutically acceptable carrier.

Still another aspect of the present invention is methods of use of 9-substituted guanine compounds according to the present invention. These methods of use include a method of stimulating regeneration of mammalian motor neurons or mammalian sensory neurons, a method of treating a disease or condition in a mammal treatable by inhibiting the activity of a monoamine oxidase, and a method of regulating calcium channel function in a mammal.

DESCRIPTION

We have developed 9-substituted guanine derivatives that are bifunctional and pass through the blood-brain barrier. In general, bifunctional 9-substituted guanine derivatives according to the present invention comprise a guanine moiety linked through its nitrogen-9 atom through a linker to a physiologically active group. The length of the linker is chosen so that both the guanine moiety and the physiologically active group can bind to two different receptors. Although a large number of linkers can be used to covalently link the guanine moiety and the physiologically active group, a particularly preferred linker incorporates a hydrocarbyl moiety that includes a carbonyl group. The carbonyl group can be present as part of a substituted aldehyde residue, as part of an ester moiety, or part of an amide moiety. Preferably, the hydrocarbyl moiety is saturated and unbranched. The end of the hydrocarbyl moiety that is terminated with the carbonyl group is linked to the physiologically active group, such as through an amide linkage. A preferred length of the hydrocarbyl moiety is two carbon atoms; this length does not include the functionalized carbon atom that contains the carbonyl group. The length of the linker can be varied according to the physiologically active group covalently linked to the guanine moiety.

Particular embodiments of the linkers and the physiologically active groups are described below.

In one embodiment of the present invention, the physiologically active group is a serotonin analogue. This 9-substituted guanine derivative is shown in formula (I). In the 9-substituted guanine derivative of formula (I), n is an integer from 1 to 6. Preferably, n is 2. $R_1$ is H, COOH, or $COOW_1$, where $W_1$ is lower alkyl, amino, or lower alkylamino. $R_2$ is H or OH.

(I)

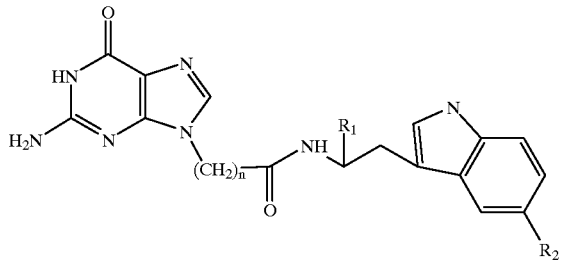

One particularly preferred compound according to the present invention incorporating a serotonin analogue is N-(2-(5-hydroxyindol-3-yl)ethyl)-3-(2-amino-6-oxohydropurin-9-yl)propanamide. In this molecule, n is 2, $R_1$ is H, and $R_2$ is OH.

Another particularly preferred molecule according to the present invention incorporating a serotonin analogue is N-(2-(indol-3-yl)ethyl)-3-(2-amino-6-oxohydropurin-9-yl) propanamide. In this molecule, n is 2, $R_1$ is H, and $R_2$ is H.

Another particularly preferred compound according to the present invention incorporating a serotonin analogue is N-(1-carboxyl)-(2-(5-hydroxyindol-)3-yl)ethyl)-3-(2-amino-6-oxohydropurin-9-yl). In this compound, n is 2, $R_1$ is COOH, and $R_2$ is OH. Other serotonin analogues can be used in 9-substituted guanine derivatives of the present invention.

Methods of use of these compounds are described below. However, one particular use of compounds according to the present invention incorporating serotonin analogs is a method of stimulating regeneration of serotonergic neurons or reestablishing homeostatic function to serotonergic neurons. This comprises a step of administering an effective amount of a guanine derivative incorporating a serotonin moiety to the mammal.

Another embodiment of a 9-substituted guanine derivative according to the present invention is a compound in which the physiologically active group is a p-aminobenzoic acid analogue. A 9-substituted guanine derivative according to the present invention incorporating a p-aminobenzoic acid analog has formula (II) wherein n is an integer from 1 to 6.

(II)

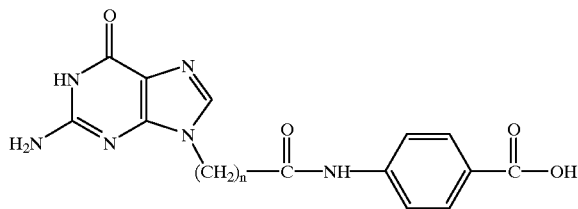

Preferably, n is 2 and the compound is N-4-carboxyphenyl-3-(2-amino-6-oxohydropurin-9-yl) propanamide.

The present invention also includes analogues of compounds of formula (II) in which the phenyl group of the p-aminobenzoic acid analog is substituted.

A number of uses for these derivatives are described below. However, one particular use is a method of stimulating regeneration of mammalian neurons comprising the step of administering an effective amount of the 9-substituted guanine derivative incorporating the p-aminobenzoic acid analogue to the mammal.

Another 9-substituted guanine derivative according to the present invention is of formula (III) wherein n is an integer from 1 to 6. Preferably, n is 2, and the compound is 3-(2-amino-6-oxohydropurin-9-yl)propanoic acid.

(III)

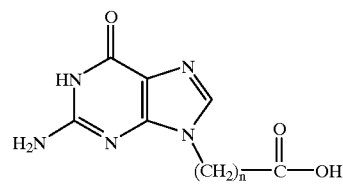

Another 9-substituted guanine derivative according to the present invention is shown in formula (IV) wherein n is an integer from 1 to 6, p is an integer from 1 to 6, and q is an integer from 1 to 3. Preferably, n is 2, p is 2, and q is 1, and the compound is N-[2-[[2-(2-oxopyrrolidin-1-yl)-1-oxoethyl]amino]ethyl] propanamide.

(IV)

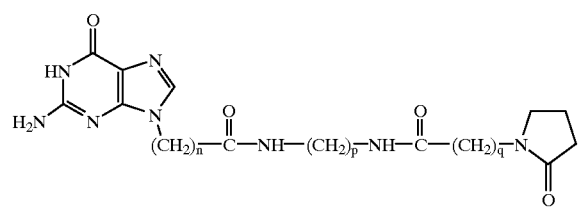

Another embodiment of a 9-substituted guanine derivative according to the present invention incorporates a dopamine analogue. This derivative is shown in formula (V). In formula (V), n is an integer from 1 to 6. $R_1$ is H, COOH, or $COOW_1$, where $W_1$ is lower alkyl amino, or lower alkylamino In formula (V), $R_2$ is H or OH. In formula (V), $R_3$ is H or OH.

(V)

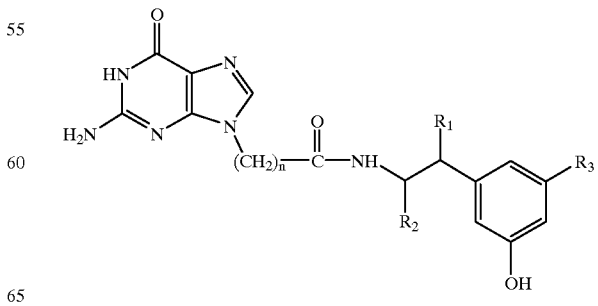

Preferably, n is 2.

Particularly preferred compounds according to the present invention incorporating dopamine analogs are N-(2-(3,4-dihydroxyphenyl)ethyl-3-(2-amino-6-oxohydropurin-9-yl) propanamide, where $R_1$ is H, $R_2$ is H, and $R_3$ is OH; and N-2-hydroxy-2-(3,4 dihydroxyphenyl)ethyl-3-(2-amino-6-oxohydropurin-9-yl)propanamide, where n is 2, $R_1$ is H, $R_2$ is OH, and $R_3$ is OH. Another compound is N-(1-carboxyl-2-(3,4 dihydroxyphenyl)ethyl-3-(2-amino-6-oxohydropurin-9-yl)propanamide. In this compound, n is 2, $R_1$ is COOH, $R_2$ is H, and $R_3$ is H.

Methods of use of these 9-substituted guanine derivatives incorporating dopamine analogues are described below. These methods of use include a method of treating a disease or condition in a mammal treatable by inhibiting the activity of a monoamine oxidase and regulating the levels of dopamine in the brain comprising the step of administering an effective amount of the 9-substituted guanine derivative incorporating a dopamine analogue to the mammal.

Another method of use of these compounds is a method of regulating calcium channel function in a mammal comprising administering an effective amount of a compound according to the present invention incorporating a dopamine analogue to a mammal to regulate calcium channel function. Dysfunction of calcium channels has been implicated in a wide spectrum of human cardiovascular (e.g., hypertension, arrythmia), respiratory (e.g., asthma), and neurological diseases (e.g., stroke, amyotrophic lateral sclerosis (ALS or Lou Gehrig's Disease), Alzheimer's Disease and migraine). Therefore, regulation of calcium channel function is important.

Another 9-substituted guanine derivative according to the present invention is an amino-substituted p-aminobenzoic acid analogue shown in formula (VI). In the compounds of formula (VI), n is an integer from 1 to 6. Preferably, n is 2. In these compounds, p is an integer from 1 to 3; preferably, p is 1. A particularly preferred amino-substituted p-aminobenzoic acid analogue according to the present invention is the compound of formula (VI) in which n is 2 and p is 1. This compound is the 1-(dimethylamino)-2-propyl ester of N-4-carboxyphenyl-3-(2-amino-6-oxohydropurin-9-yl)propanamide.

compound according to the present invention when n is 2 and p is 1 is N-(1-ethylpyrrolidine-2-yl)methyl-3-(2-amino-6-oxohydropurin-9-yl)propanamide.

(VII)

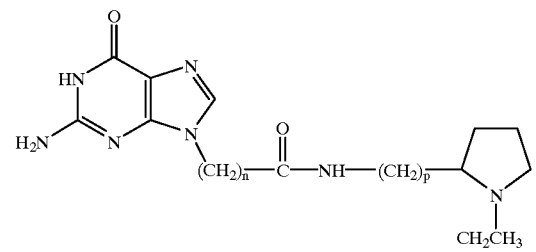

Another embodiment of a 9-substituted guanine derivative according to the present invention is a 4-morpholinyl analogue as shown in formula (VIII). In formula (VIII), n is an integer from 1 to 6; preferably, n is 2. In this formula, p is an integer from 1 to 6; preferably, p is 2 or 3. A particularly preferred 9-substituted guanine derivative according to the present invention is N-(2-(4-morpholinyl)-ethyl)-3-(2-amino-6-oxohydropurin-9-yl)propanamide; in this compound n is 2 and p is 2. Another particularly preferred 9-substituted guanine derivative according to the present invention is N-(3-(4-morpholinyl)-propyl)-3-(2-amino-6-oxohydropurin-9-yl)propanamide; in this compound, n is 2 and p is 3.

(VIII)

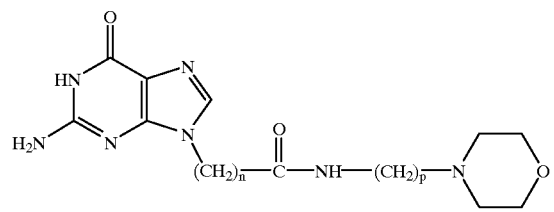

Another embodiment of a 9-substituted guanine derivative according to the present invention is a (VI)

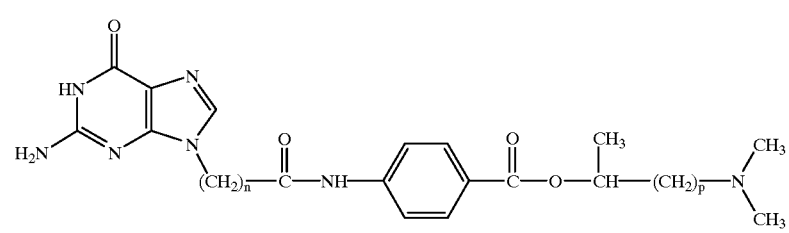

Another embodiment of the present invention is a 9-substituted guanine analogue in which the guanine is linked to a 1-ethylpyrrolidine moiety as shown in formula (VII). In the compound of formula (VII), n is an integer from 1 to 6. Preferably, n is 2. In this compound, p is an integer from 1 to 3; preferably, p is 1. A particularly preferred 1-benzylpiperidinyl analogue as shown in formula (IX). In the compound of formula (IX), n is an integer from 1 to 6; preferably, n is 2. A particularly preferred 9-substituted guanine derivative according to the present invention N-(1-benzylpiperidin-4-yl)-3-(2-amino-6-oxohydropurin-9-yl) propanamide.

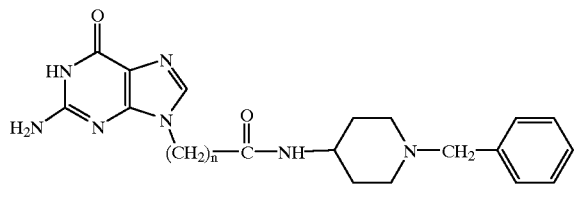

(IX)

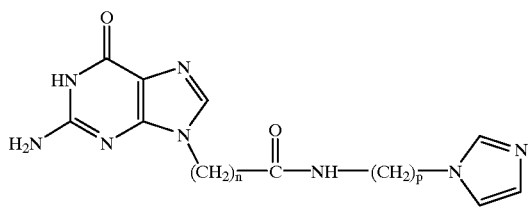

(XII)

Another embodiment of 9-substituted guanine derivatives according to the present invention is a 2-oxopyrrolidinyl analogue as shown in formula (X). In compounds of formula (X), n is an integer from 1 to 6. Preferably, n is 2. In these compounds, p is an integer from 1 to 6; preferably, p is 3. A particularly preferred compound according to the present invention is N-[3-(2-oxopyrrolidin-1-yl)propyl]-3-(2-amino-6-oxohydropurin-9-yl)propanamide. In this compound, n is 2 and p is 3.

Another embodiment of the present invention is a 2-methylpiperidine analogue as shown in formula (XIII). In compounds of formula (XIII), n is an integer from 1 to 6; preferably, n is 2. In these compounds, p is an integer from 1 to 6; preferably, p is 3. A particularly preferred compound according to the present invention is N-[3-(2-methylpiperidin-1-yl)propyl]-3-(2-amino-6-oxohydropurin-9-yl)propanamide.

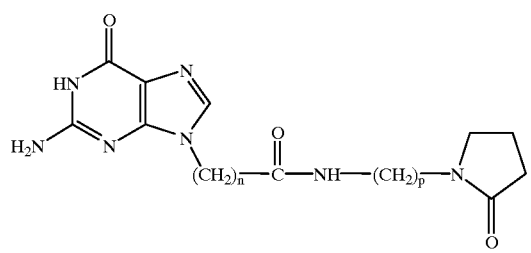

(X)

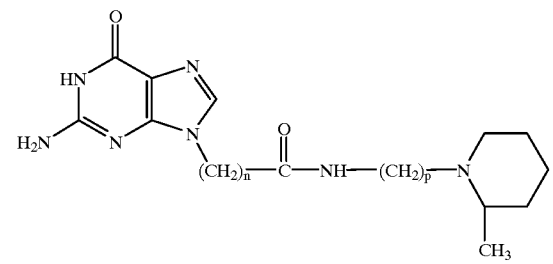

(XIII)

Another embodiment of the present invention is a 1-methylpyrrole analogue as shown in formula (XI). In the compounds of formula (XI), n is an integer from 1 to 6; preferably n is 2. In these compounds, p is an integer from 1 to 6; preferably, p is 2. A particularly preferred compound according to the present invention is N-[2-(1-methylpyrrol-2-yl)ethyl]-3-(2-amino-6-oxohydropurin-9-yl)propanamide.

Another embodiment of the present invention is a 1-methylpyrrolidine analogue of formula (XIV). In compounds of formula (XIV), n is an integer from 1 to 6; preferably, n is 2. In this formula, p is an integer from 1 to 6; preferably, p is 2. A particularly preferred compound according to the present invention is N-[2-(1-methylpyrrolidin-2-yl)ethyl]-3-(2-amino-6-oxohydropurin-9-yl)propanamide.

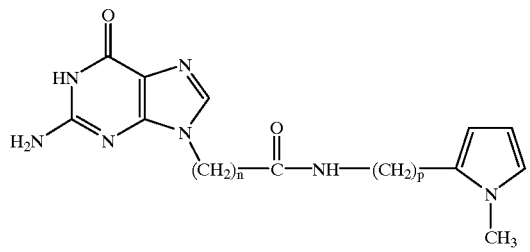

(XI)

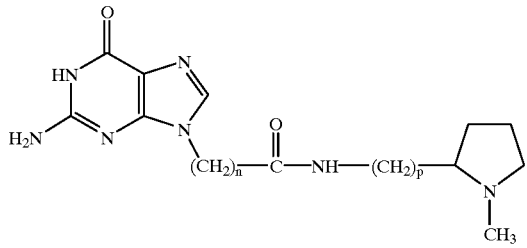

(XIV)

Another embodiment of 9-substituted guanine derivatives according to the present invention is an imidazole analogue as shown in formula (XII). As shown in formula (XII), n is an integer from 1 to 6; preferably, n is 2. In this formula, p is an integer from 1 to 6; preferably, p is 3. A particularly preferred compound according to the present invention is N-[3-(1-imidazolyl)propyl]-3-(2-amino-6-oxohydropurin-9-yl)propanamide.

Another embodiment of a 9-substituted guanine derivative according to the present invention is a 2-hydroxyethyl analogue as shown in formula (XV). In compounds of formula (XV), n is an integer from 1 to 6; preferably, n is 2. A particularly preferred compound is N-(2-hydroxyethyl)-3-(2-amino-6-oxohydropurin-9-yl)propanamide.

(XV)

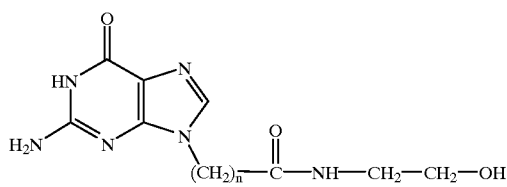

(XVIII)

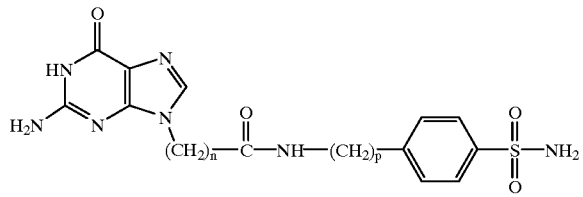

Another embodiment of a 9-substituted guanine derivative according to the present invention is a 2-hydroxyethoxy analogue as shown in formula (XVI). In compounds of formula (XVI), n is an integer from 1 to 6; preferably, n is 2. A particularly preferred compound is N-[2-2-hydroxyethyl)ethyl]-3-(2-amino-6-oxohydropurin-9-yl)propanamide.

Another embodiment of a 9-substituted guanine derivative according to the present invention is a (2-hydroxy-1-methyl-2-phenyl)ethyl analogue as shown in formula (XIX). In compounds of formula (XIX), n is an integer from 1 to 6; preferably, n is 2. A particularly preferred compound according to the present invention is N-[(2-hydroxy-1-methyl-2-phenyl)ethyl]-3-(2-amino-6-oxohydropurin-9-yl)propanamide.

(XVI)

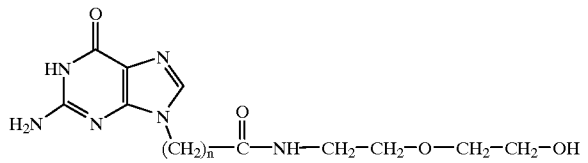

(XIX)

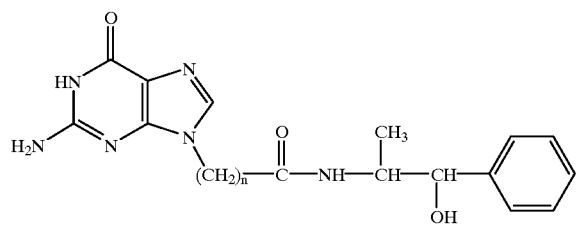

Another embodiment of a 9-substituted guanine derivative according to the present invention is a 2-hydroxyethylaminoethyl analogue as shown in formula (XVII). In compounds of formula (XVII), n is an integer from 1 to 6; preferably, n is 2. A particularly preferred compound according to the present invention is N-[2-[(2-hydroxethyl)amino]ethyl]-3-(2-amino-6-oxohydropurin-9-yl)propanamide.

Another embodiment of a 9-substituted guanine derivative according to the present invention is an oxoethylaminoalkyl analogue as shown in formula (XX). In compounds of formula (XX), n is an integer from 1 to 6; preferably, n is 2. In these compounds, p is an integer from 1 to 6; preferably, p is 2. A particularly preferred compound according to the present invention is N-[2-[(1-oxoethyl)amino]ethyl]-3-(2-amino-6-oxohydropurin-9-yl)propanamide.

(XVII)

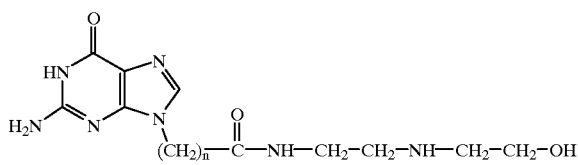

Another embodiment of a 9-substituted guanine derivative according to the present invention is a 4-aminosulfonylphenylalkyl analogue as shown in formula (XVIII). In compounds of formula (XVIII), n is an integer from 1 to 6; preferably, n is 2. In these compounds, p is an integer from 1 to 6; preferably, p is 2. A particularly preferred compound according to the present invention is N-[2-(4-aminosulfonylphenyl)ethyl]-3-(2-amino-6-oxohydropurin-9-yl)propanamide.

(XX)

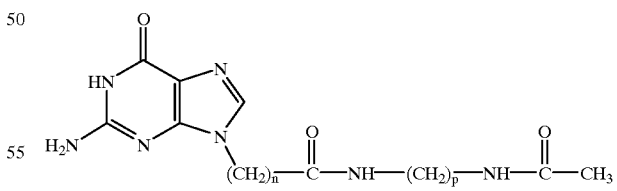

Another embodiment of a 9-substituted guanine derivative according to the present invention is an 1,4-dioxa-8-azaspiro[4.5]decyl analogue as shown in formula (XXI). In compounds of formula (XXI), n is an integer from 1 to 6; preferably, n is 2. A particularly preferred compound according to the present invention is 1-[1,4-dioxa-8-azaspiro-[4.5]dec-8-yl]-3-(2-amino-6-oxohydropurin-9-yl)propanone.

(XXI)
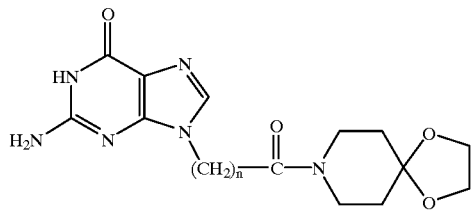

(XXIV)
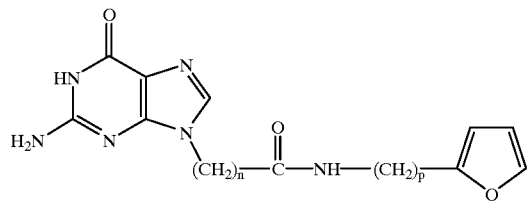

Another embodiment of a 9-substituted guanine derivative according to the present invention is an aminoalkyl analogue of formula (XXII). In compounds of formula (XXII), n is an integer from 1 to 6; preferably, n is 2. In these compounds, p is an integer from 1 to 6; preferably, p is 2. A particularly preferred compound according to the present invention is N-(2-aminoethyl)-3-(2-amino-6-oxohydropurin-9-yl)propanamide.

Another embodiment of a 9-substituted guanine derivative according to the present invention is a 2,3-dihydroxypropyl analogue as shown in formula (XXV). In these compounds, n is an integer from 1 to 6; preferably, n is 2. A particularly preferred compound is N-(2,3-dihydroxyprop-1-yl)-3-(2-amino-6-oxohydropurin-9-yl)propanamide.

(XXII)
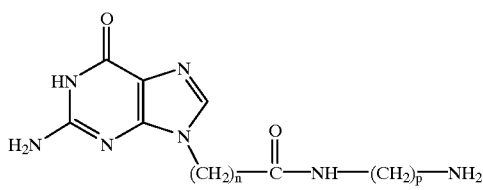

(XXV)
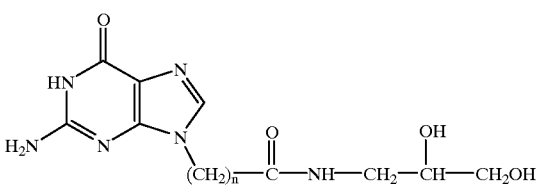

Another embodiment of a 9-substituted guanine derivative according to the present invention is a 2-hydroxypropyl analogue as shown in formula (XXIII). In compounds of formula (XXIII), n is an integer from 1 to 6; preferably, n is 2. A particularly preferred compound according to the present invention is N-(2-hydroxypropyl)-3-(2-amino-6-oxohydropurin-9-yl)propanamide.

Another embodiment of a 9-substituted guanine derivative according to the present invention is a (2-pyridinyl)alkyl analogue according to formula (XXVI). In compounds of formula (XXVI), n is an integer from 1 to 6; preferably, n is 2. In these compounds, p is an integer from 1 to 3; preferably, p is 1. A particularly preferred compound according to the present invention is N-[(2-pyridinyl)methyl]-3-(2-amino-6-oxohydropurin-9-yl)propanamide.

(XXIII)
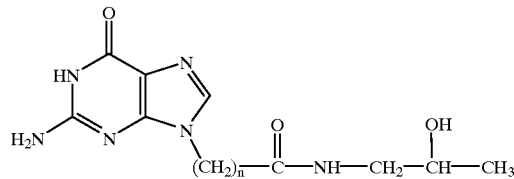

(XXVI)
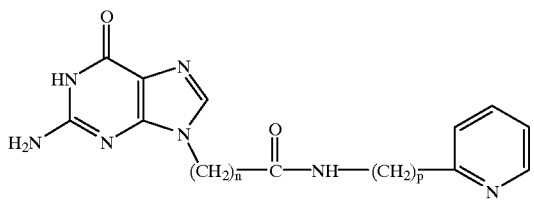

Another embodiment of a 9-substituted guanine derivative according to the present invention is a (2-furanyl)alkyl analogue as shown in formula (XXIV). In compounds of formula (XXIV), n is an integer from 1 to 6; preferably, n is 2. In these compounds, p is an integer from 1 to 3; preferably, p is 1. A particularly preferred compound according to the present invention is N-[(2-furanyl)methyl]-3-(2-amino-6-oxohydropurin-9-yl)propanamide.

Another embodiment of a 9-substituted guanine derivative according to the present invention is a 2-diethylaminoalkyl analogue as shown in formula (XXVII). In these compounds, n is an integer from 1 to 6; preferably, n is 2. In these compounds, p is an integer from 2 to 6; preferably, p is 2. A particularly preferred compound according to the present invention is N-[(2-diethylamino)ethyl]-3-(2-amino-6-oxohydropurin-9-yl)propanamide.

(XXVII)

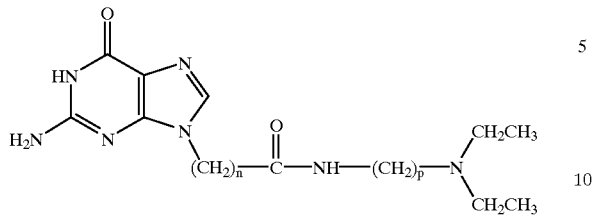

Another embodiment of a 9-substituted guanine derivative according to the present invention is an oxopyrrolidinyl-oxoalkyl-aminoalkyl analogue as shown in formula (XXVIII). In compounds of formula (XXVIII), n is an integer from 1 to 6; preferably, n is 2. In these compounds, p is an integer from 1 to 6; preferably, p is 2. In these compounds, q is an integer from 1 to 3; preferably, q is 1. A particularly preferred compound according to the present invention is N-[2-[[2-(2-oxopyrrolidin-1-yl)-1-oxoethyl]aminoethyl]-3-(2-amino-6-oxohydropurin-9-yl)propanamide.

(XXVIII)

Another embodiment of a 9-substituted guanine derivative according to the present invention is a piperonyl analogue as shown in formula (XXIX). In compounds of formula (XXIX), n is an integer from 1 to 6; preferably, n is 2. A particularly preferred compound is N-piperonyl-3-(2-amino-6-oxohydropurin-9-yl)propanamide.

(XXIX)

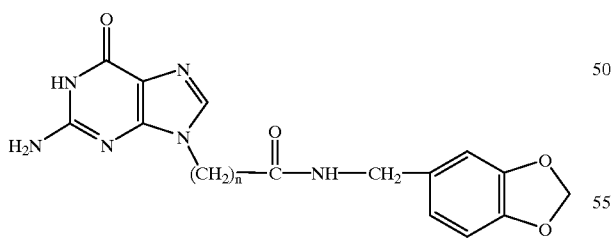

Another embodiment of a 9-substituted guanine derivative according to the present invention is a pyrrolidinyl analogue according to formula (XXX). In compounds according to formula (XXX), n is an integer from 1 to 6; preferably, n is 2. In these compounds, p is an integer from 1 to 6; preferably, p is 2. A particularly preferred compound according to the present invention is N-[(1-pyrrolidinyl)ethyl]-3-(2-amino-6-oxohydropurin-9-yl)propanamide.

(XXX)

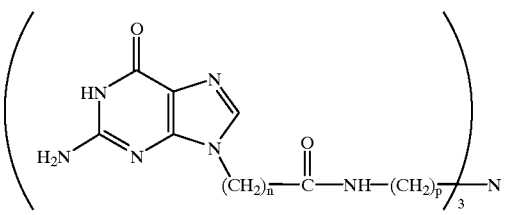

Another embodiment of a 9-substituted guanine derivative according to the present invention is a trisubstituted amine analogue as shown in formula (XXXI). In the compounds of formula (XXXI), n is an integer from 1 to 6; preferably, n is 2. In these compounds, p is an integer from 2 to 6; preferably, p is 2. A particularly preferred compound according to the present invention is N,N',N",-tri[2-[3-(2-amino-6-oxohydropurin-9-yl)-1-oxopropyl]aminoethyl]amine.

(XXXI)

Another embodiment of a 9-substituted guanine derivative according to the present invention is a piperidinylalkyl analogue as shown in formula (XXXII). In the compounds of formula (XXXII), n is an integer from 1 to 6; preferably, n is 2. In this compound, p is an integer from 2 to 6; preferably, p is 2. A preferred compound is N-[[2-(1-piperidinyl)ethyl]-3-(2-amino-6-oxohydropurin-9-yl)propanamide.

(XXXII)

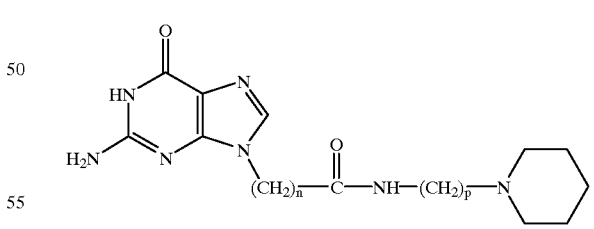

Another embodiment of 9-substituted guanine derivatives according to the present invention is a diethanolaminoalkyl analogue as shown in formula (XXXIII). In compounds of formula (XXXIII), n is an integer from 1 to 6; preferably, n is 2. In these compounds, p is an integer from 2 to 6; preferably, p is 2. A particularly preferred compound according to the present invention is N-[2-(2,2'-diethanolamino)ethyl]-3-(2-amino-6-oxohydropurin-9-yl)propanamide.

(XXXIII)

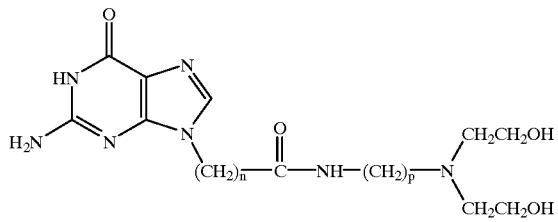

(XXXVI)

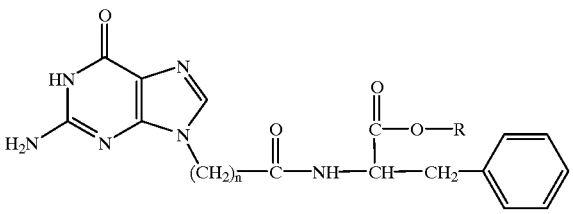

Another embodiment of 9-substituted guanine derivatives according to the present invention is an indolylalkyl analogue according to formula (XXXIV). In compounds of formula (XXXIV), n is an integer from 1 to 6; preferably, n is 2. In compounds of formula (XXXIV), p is an integer from 2 to 6; preferably, p is 2. A particularly preferred compound is N-[2-(1H-indol-3-yl)ethyl]-3-(2-amino-6-oxohydropurin-9-yl)propanamide.

Another embodiment of a 9-substituted guanine derivative according to the present invention is a N-(1-carboxy-2-phenyl)ethyl analogue as shown in formula (XXXVII). In compounds of formula (XXXVII), n is an integer from 1 to 6; preferably, n is 2. A particularly preferred compound is N-(1-carboxy-2-phenyl)ethyl-3-(2-amino-6-oxohydropurin-9-yl)propanamide.

(XXXIV)

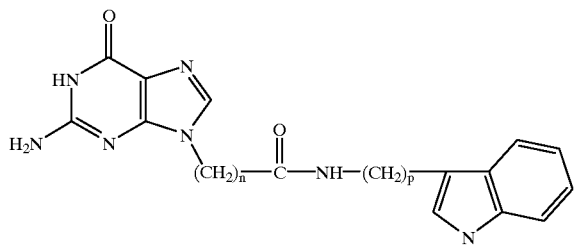

(XXXVII)

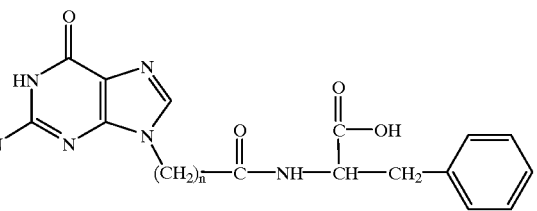

Another embodiment of a 9-substituted guanine derivative according to the present invention is a carboalkoxyphenyl analogue as shown in formula (XXXV). In compounds of formula (XXXV), n is an integer from 1 to 6; preferably n is 2. In compounds of formula (XXXV), R is a lower alkyl residue of from $C_1$ to $C_6$; preferably, R is ethyl. A particularly preferred compound is N-(4-carboethoxyphenyl)-3-(2-amino-6-oxohydropurin-9-yl)propanamide.

Another embodiment of a 9-substituted guanine derivative according to the present invention is a deoxyglucopyranosyl analogue according to formula (XXXVIII). In compounds of formula (XXXVIII), n is an integer from 1 to 6; preferably, n is 2. A particularly preferred compound according to the present invention is N-[2-(2-deoxyglucopyranosyl)]-3-(2-amino-6-oxohydropurin-9-yl)propanamide.

(XXXV)

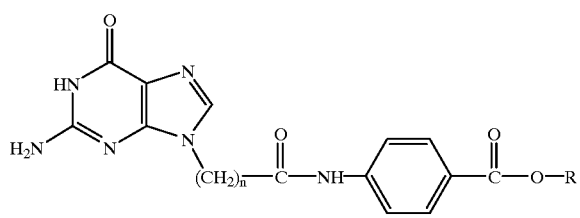

(XXXVIII)

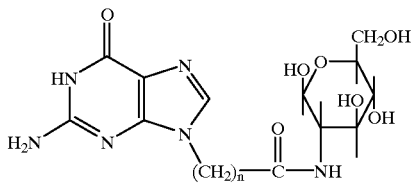

Another embodiment of a 9-substituted guanine derivative according to the present invention is an N-(1-carboalkoxy-2-phenyl)ethyl analogue as shown in formula (XXXVI). In compounds of formula (XXXVI), n is an integer from 1 to 6; preferably, R is 2 In compounds of formula (XXXVI), R is a lower alkyl residue of from $C_1$ to $C_6$; preferably, R is ethyl. A particularly preferred compound according to the present invention is N-(1-carboethoxy-2-phenyl)ethyl-3-(2-amino-6-oxohydropurin-9-yl)propanamide.

Another embodiment of the present invention is a 1-oxopropylaminoalkylamino-2-hydroxy-4-oxo-N,N,N-trimethyl-1 butanaminium chloride analogue as shown in formula (XXXIX). In compounds of formula (XXXIX), n is an integer from 1 to 6; preferably, n is 2. In compounds of formula (XXXIX), p is an integer from 1 to 6; preferably, p is 2. A particularly preferred compound is 4-[[2-[[3-(2-amino-6-oxohydropurin-9-yl]-1-oxopropyl]amino]ethyl]amino]-2-hydroxy-4-oxo-N,N,N-trimethyl-1-butanaminium chloride.

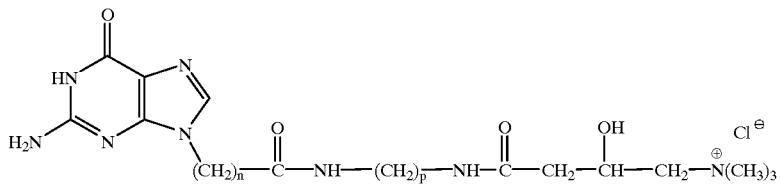

(XXXIX)

Another embodiment of a 9-substituted guanine derivative according to the present invention is an N-carboalkoxyalkyl analogue as shown in formula (XL). In compounds of formula (XL), n is an integer from 1 to 6; preferably, n is 2. In these compounds, p is an integer from 2 to 6; preferably, p is 3. In these compounds, R is a lower alkyl residue of 1 to 3 carbon atoms; preferably, R is methyl. A particularly preferred compound is N-[(3-carboethoxy) propyl]-3-(2-amino-6-oxohydropurin-9-yl)propanamide.

p is 3. A particularly preferred compound is N-[(3-sulfo) propyl]-3-(2-amino-6-oxohydropurin-9-yl)propanamide.

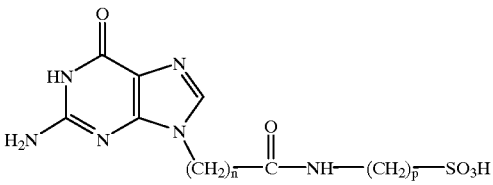

(XLI)

(XL)

Another embodiment of a 9-substituted guanine derivative according to the present invention is a N-sulfoalkyl analogue as shown in formula (XLI). In compounds of formula (XLI), n is an integer from 1 to 6; preferably, n is 2. In the compound, p is an integer from 2 to 6; preferably, Another embodiment of a 9-substituted guanine derivative according to the present invention is a N-diethylaminoethyl benzamide hydrochloride analogue as shown in formula (XLII). In compounds of formula (XLII), n is an integer from 1 to 6; preferably, n is 2. In these compounds, p is an integer from 1 to 6; preferably, p is 2. A particularly preferred compound according to the present invention is 4-[[3-(2-amino-6-oxohydropurin-9-yl)-1-oxopropyl]amino]-N-[(diethylamino)ethyl] benzamide hydrochloride.

(XLII)

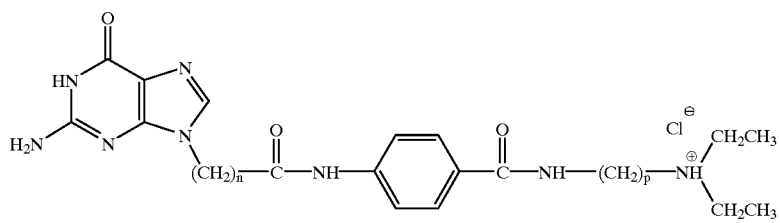

Another embodiment of a 9-substituted guanine derivative according to the present invention is an oxothiolanyl analog as shown in formula (XLIII). In formula (XLIII), n is an integer from 1 to 6; preferably, n is 2. A particularly preferred compound according to the present invention is N-(2-oxothiolan-3-yl)-3-(2-amino-6-oxohydropurin-9-yl)propanamide.

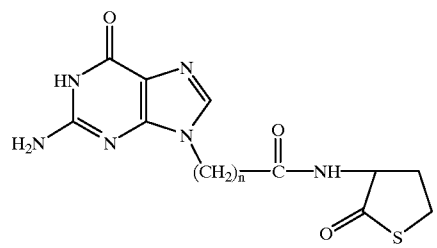

(XLIII)

Another embodiment of a 9-substituted guanine derivative according to the present invention is a 1-phenyl-4-oxo-1,3,8-triazaspiro[4.5]decyl analogue as shown in formula (XLIV). In compounds of formula (XLIV), n is an integer from 1 to 6. Preferably, n is 2. A particularly preferred compound according to the present invention is 3-(2-amino-6-oxohydropurin-9-yl)-1-(1-phenyl-4-oxo-1,3,8-triazaspiro[4.5]dec-8-yl)propanone.

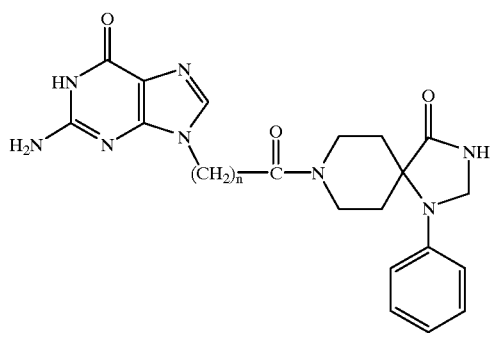

(XLIV)

Another embodiment of a 9-substituted guanine derivative according to the present invention is a 1,2,3,4-tetrahydro-2-azacarbazoyl analogue as shown in formula (XLV). In compounds of formula (XLV), n is an integer from 1 to 6; preferably, n is 2. A particularly preferred compound according to the present invention is 3-(2-amino-6-oxohydropurin-9-yl)-1-(1,2,3,4-tetrahydro-2-azacarbazo-2-yl)propanone.

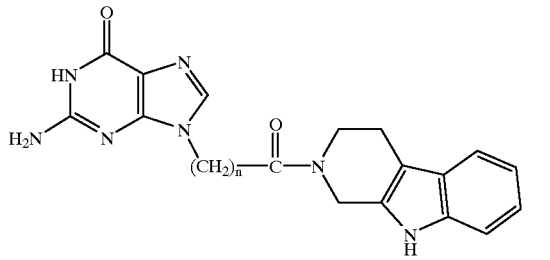

(XLV)

Another embodiment of a 9-substituted guanine derivative according to the present invention is an N-niethyl-N-(2-(3,4-dihydroxyphenyl)-2-hydroxyethyl) analogue as shown in formula (XLVI). In formula (XLVI), n is an integer from 1 to 6; preferably n is 2. A particularly preferred compound according to the present invention is N-[2-(3,4-dihydroxyphenyl)-2-hydroxyethyl]-N-methyl-3-(2-amino-6-oxohydropurin-9-yl)propanamide.

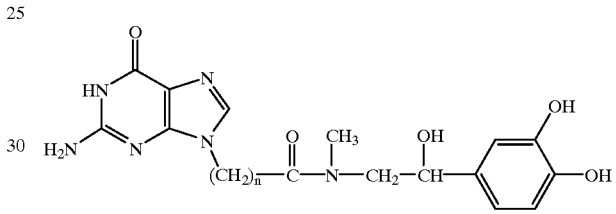

(XLVI)

Another embodiment of a 9-substituted guanine derivative according to the present invention is a phenylimidazolyl analog as shown in formula (XLVII). In compounds of formula (XLVII), n is an integer from 1 to 6; preferably, n is 2. A particularly preferred compound according to the present invention is 3-(2-amino-6-oxohydropurin-9-yl)1-(2-phenylimidazo-1-yl)propamone.

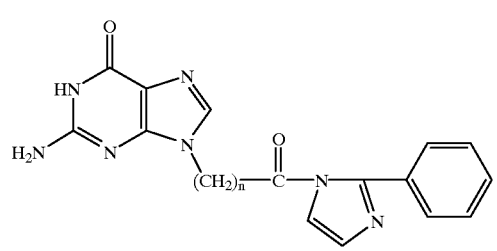

(XLVII)

Another embodiment of a 9-substituted guanine derivative according to the present invention is a piperidine carboxylate analogue as shown in formula (XLVIII). In compounds of formula (XLIVIII), n is an integer from 1 to 6; preferably, n is 2. In these compounds, R is a lower alkyl of 1 to 6 carbons; preferably, R is ethyl. A particularly preferred compound according to the present invention is ethyl 1-[3-(2-amino-6-oxohydropurin-9-yl)-1-oxopropyl]-3-piperidine carboxylate.

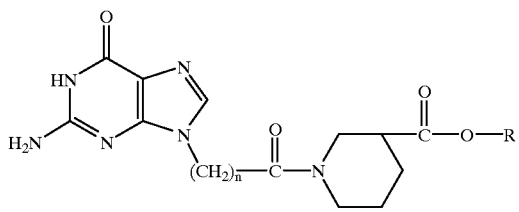

(XLVIII)

Another embodiment of a 9-substituted guanine derivative according to the present invention is a dimethylaminocarbopropoxyphenyl analogue as shown in formula (XLIX). In compounds of formula (XLIX), n is an integer from 1 to 6; preferably, n is 2. A particularly preferred compound according to the present invention is N-(4-(1-dimethylamino-2-carbopropoxy)phenyl)-3-(2-amino-6-oxohydropurin-9-yl)propanamide.

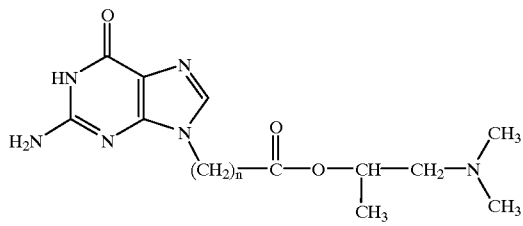

(XLIX)

In accordance with the teaching of the present invention, it is generally preferred that the individual pharmacophores or active moieties be covalently linked by a chemical bridging group. Preferably, the bridging group contains biodegradable linkages such as single or multi-amide or peptide like linkages. In this manner, it is possible for the chemical structural moieties of the compounds of the present invention to function independently following hydrolysis or other cleavage of the chemical bridging group. Exemplary bridging groups in accordance with the teachings of the present invention are propionic acid and butyric acid or derivatives thereof, such as propanamide and analogues. Though it was believed that such biodegradable linkages would be hydrolyzed by known proteolytic enzymes present in the body to allow such independent function to occur, in view of the completely unexpected biological activities observed for these compounds, it is now proposed that the respective chemical moieties of each compound may remain linked. As a result, it is believed that these linked, biologically active chemical moieties are able to simultaneously interact with adjacent or structurally close receptor sites on individual cells. More particularly, the uniquely dose-dependent activities, synergistic biological properties, and diverse specific biological effects of the compounds of the present invention are indicative of unusual and unexpected interactive mechanisms which cannot be explained by simple biodegradation of the chemical linking group.

Exemplary pharmacophores for practicing the present invention can be selected in those chemical moieties exhibiting biological activity in the following therapeutic classes: analgesic, antihelminthic, anti-ulcer, antibacterial, antibiotic, anticonvulsant, antifungal, antihypertension, antimalarial, antineoplastic, antiarthritic, bronchodilator, cardiovascular, immunologic, antidepressant, diuretic, diuretic-carbonic anhydrase inhibitor, muscle relaxant, neurologic, neurotransmitter, anti-parkinsonism, psychostimulant and sympathomimetic. However, those skilled in the art will appreciate that other therapeutic classes of pharmacophores are contemplated as being within the scope of the present invention.

Thus, the multifunctional compounds of the present invention can be formed from chemically bridged combinations of moieties such as aspirin, piperazine, cimetidine, ranitidine, sulfamethoxazole, sulfisoxazole, penicillin G, cephalosporin C, tetracycline, phenytoin, fluorocytosine, aminobutyric acid, primaquine, pyrimethamine, methotrexate, naproxen, ibuprofen, epinephrine, ephedrine, theophylline, captopril, acebutol, flecainide, mexiletine, procainamide, tocainide, carnitine, chlordiazepoxide, desipramine, maprotiline, meprobamate, nortriptyline, protriptyline, tranylcypromine, amiloride, triamnterene, ethacrynic acid, acetazolamide, prazosin, baclofen, hypoxanthine, 5-hydroxytryptamine, levodopa, methamphetamine, methylphenidate, pemoline, dextroamphetamine, dopamine, or structurally similar biologically active compounds.

Accordingly, in accordance with the teachings of the present invention, it is particularly desirable to produce compounds that are designed to correct functional defects in both immune and nerve cells. As those skilled in the art will appreciate, because specific neurological and immune defects or deficiencies are known in both Alzheimer's disease and in conjunction with the neurological aspects of HIV infection, these syndromes or conditions are principal targets of the exemplary embodiments of the present invention. Similarly, the diseases of schizophrenia and neuroimmunological deficiencies associated with aging are also targets of these embodiments. It should be emphasized that the following, non-limiting examples are illustrative of the present invention and are in no way intended to limit the scope of the present invention to neuroimmunologic compounds.

II. PHARMACEUTICAL COMPOSITIONS

Another aspect of the present invention is pharmaceutical compositions. A pharmaceutical composition according to the present invention comprises:

(1) an effective amount of a 9-substituted guanine derivative according to the present invention as described above; and (2) a pharmaceutically acceptable carrier.

A pharmaceutically acceptable carrier can be chosen from those generally known in the art, including, but not limited to, human serum albumin, ion exchangers, alumina, lecithin, buffer substances such as phosphates, glycine, sorbic acid, potassium sorbate, and salts or electrolytes such as potassium sulfate. Other carriers can be used.

III. METHODS OF USE

A. Monoamine Oxidase Inhibition

Yet another aspect of the present invention is a method of treating a disease or condition in a mammal treatable by inhibiting the activity of a monoamine oxidase.

This method comprises a step of administering an effective amount of a 9-substituted guanine derivative of the present invention to the mammal. The 9-substituted guanine derivative that can be used is a compound of formula (V), in which n is an integer from 1 to 6; $R_1$ is H, COOH, or $COOW_1$, where $W_1$ is lower alkyl, amino, or lower alkylamino; $R_2$ is H or OH; $R_3$ is H or OH. Alternatively, the 9-substituted guanine derivative that can be used is a compound of formula (I), in which n is an integer from 1 to 6; $R_1$ is H, COOH, or $COOW_1$, where $W_1$ is lower alkyl, amino, or lower alkylamino; and $R_2$ is H or OH. The amount that is an effective amount can be determined from enzyme assays as an amount that produces a detectable inhibition of either monoamine oxidase A or monoamine oxidase B or both enzymes in an enzyme assay set forth below.

To carry out these enzyme assays, the following protocol can be used. The recitation of this protocol is only exemplary and is non-limiting; other protocols are known in the art and can be used.

Mice (3–5 mice) are sacrificed by cervical dislocation. The brains are isolated and placed immediately in 10 mL cold isolation medium (IM) (500 μM EDTA, 5 mM HEPES, 0.25 M sucrose, and 10 mg/L bovine serum albumin (BSA)). The brains are minced and rinsed twice with 10 mL IM. The brains are then homogenized (5–6 strokes) in 10 mL IM. A volume (20 mL) of IM is then added and the homogenized preparation is centrifuged 8–10 minutes at 600×g at 4° C. The supernatant is transferred to a new tube. The pellet is resuspended in 30 mL IM and is centrifuged again for 8 minutes at 600×g at 4° C. The supernatant is transferred to a new tube and the pellet is discarded. Both supernatants are centrifuged for 10 min at 12,000×g at 4° C. The supernatant is discarded, the pellet is dislodged with a glass rod, and both pellets are resuspended in 5 mL IM and are combined. A volume of IM (20 mL) is added and the suspension is centrifuged for 10 min at 12,000×g at 4° C. The supernatants are discarded. The pellets are dislodged with a glass rod and resuspended in 2–4 mL IM and are stored on wet ice during the course of the experiments.

The compounds tested are predissolved in dimethyl sulfoxide (DMSO) and are further diluted with water as required.

For the enzyme assays, 1.0 mL to 1.5 mL 50 mM sodium phosphate, pH 7.4 containing 5 μM scopoletin and 2 U/mL horseradish peroxidase) are aliquoted in the wells of a Falcon 24-well plate (reaction mixture or RM). Mitochondrial protein (0.22–0.24 mg/niL final concentration) is added, and the reaction mixtures are preincubated approximately 6 minutes with 16 μM pargyline (monoamine oxidase B inhibitor) and 166 μM clorgyline (monoamine oxidase A inhibitor) or 2–150 μM of the tested 9-substituted guanine analogues or the corresponding volume of water containing 1–5% DMSO respectively at 37° C. The preincubation is carried out in the Cytofluor® 4000 (PerSeptive Biosystems) and the baseline fluorescence at $\lambda_{ex}$=360 nm and $\lambda_{em}$=460 is recorded. After 6 min, the reading is interrupted and 150–166 μM tyramine (monoamine oxidase A and monoamine oxidase B substrate) or the corresponding amount of water are added according to the plate layout. The reading is continued for approximately 30 minutes at 3-minute intervals. The rate of the fluorescence decrease during this time is used to determine the effect of the tested compounds on the catalytic activity of both enzyme isoforms. Each plate contains a positive control containing the inhibitors for monoamine oxidase A or B respectively as well as a negative control without enzyme substrate. All determinations are in duplicates on the plate.

Determination of the protein concentration is carried out according to the manufacturer's instructions (Sigma, St. Louis, Mo.) for the bicinchoninic acid (BCA) protein determination.

The most effective amount of administration and dosage regimen for the 9-substituted guanine derivative as used in the methods of the present invention depend on the severity and course of the disease, the patient's health, the response to treatments, other drugs being administered and the response to them, pharmacokinetic considerations such as the condition of the patient's liver and/or kidneys that can affect the metabolism and/or secretion of the administered 9-substituted guanine derivatives, and the judgment of the treating physician. Accordingly, the dosages should by titrated to the individual patient.

Among the diseases and conditions for which monoamine oxidase inhibitors are clinically indicated are psychological and psychiatric conditions such as depression, panic disorders, and obsessive-compulsive disorder; chronic pain disorders such as diabetic and other peripheral neuropathic syndromes and fibromyalgia; peptic ulcer and irritable bowel syndrome; chronic fatigue, cataplexy; sleep apnea; migraine; and Parkinson's disease. Such monoamine oxidase inhibitors may also be useful for other conditions.

The mammal can be a human or other socially or economically important mammal such as a dog, a cat, a horse, a cow, a pig, or a sheep. The method of the present invention is not limited to treatment of humans.

Another aspect of method of use of the 9-substituted guanine derivatives according to the present invention is a method of stimulating regeneration of a mammalian neuron comprising the step of administering an effective amount of a 9-substituted guanine derivative of the present invention to the mammal. The 9-substituted guanine derivative is one of formula (II) wherein n is an integer from 1 to 6.

Exemplary dosages in accordance with the teachings of the present invention for these compounds range from 0.01 mg/kg to 60 mg/kg, though alternative dosages are contemplated as being within the scope of the present invention.

Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

The administration of 9-substituted guanine derivatives according to the present invention is believed to increase the level of mRNA encoding at least one neurotrophic factor in a tissue that is in chemical communication with the motoneuron. The neurotrophic factor stimulates the growth of neurons.

The neurotrophic factor can be one of nerve growth factor, NT-3, brain-derived neurotrophic factor (BDNF), and ciliary neurotrophic factor (CNTF); the neurotrophic factor can also be another neurotrophic factor as known in the art.

Functional nerve growth factor is a non-covalently linked parallel homodimer. The structure of nerve growth factor consists of three anti-parallel pairs of β-strands together forming a flat surface through which the two subunits associate.

The amino acid sequence for human nerve growth factor and mouse nerve growth factor is known. This molecule is described in R. E. Callard & A. J. H. Gearing, "The Cytokine Facts Book" (Academic Press, London, 1994), pp. 191–198, incorporated herein by this reference.

The growth factor NT-3 also promotes the survival and outgrowth of neural crest-derived sensory and sympathetic neurons. The structure of this molecule is known; its amino acid sequence is identical in the human and mouse. The structure has 60% β-sheet secondary structure and exists as a tightly linked homodimer. NT-3 is described in R. E.

Callard & A. J. H. Gearing, "The Cytokine Facts Book" (Academic Press, London, 1994), pp. 199–200, incorporated herein by this reference.

Brain derived neurotrophic factor also promotes the survival of neuronal populations located either in the central nervous system or directly connected to it. It helps to maintain neurons and their differentiated phenotype in the adult. The amino acid sequence is known for human and mouse BDNF. The molecule has 70% β-sheet secondary structure and is expressed as a tightly associated homodimer. Properties of this molecule are described in R. E. Callard & A. J. H. Gearing, "The Cytokine Facts Book" (Academic Press, London, 1994), pp. 99–100, incorporated herein by this reference.

Ciliary neurotrophic factor also promotes the survival and/or differentiation of neuronal cells. CNTF has no homology with NGF, BDNF, and NT-3. The absence of a signal peptide in N-linked glycosylation sites in CNTF is consistent with its being a cytosolic protein. The three-dimensional structure of CNTF is not known, but it has significant homologies with other cytokines, such as IL-6, LIF, oncostatin M, and G-CF. It is thought that these molecules share a four-helix bundle structure. The amino acid sequences of human CNTF and rat CNTF are known. Although these sequences are similar, they are not identical. Further information about CNTF is given at R. E. Callard & A. J. H. Gearing, "The Cytokine Facts Book" (Academic Press, London, 1994), pp. 104–105, incorporated herein by this reference.

Although Applicant does not intend to be bound by this theory, the increase of the level of mRNA of these neurotrophic factors brought about by the methods of the present invention is believed to promote neuronal survival.

The term "effective amount" as used herein in the specification means an amount of the compound that causes a detectable increase in the messenger RNA level of at least one of the recited neurotrophic factors. Methods of measuring the mRNA levels typically involve hybridization to probes containing mRNA-specific sequences and detecting the quantity of hybrid nucleic acid formed. The hybrid nucleic acid formed is typically detected by a label incorporated in one of the two nucleic acid strands forming the hybrid. This label can be radioactive or non-radioactive; if non-radioactive it can be fluorescent, chemiluminescent, bioluminescent, enzymatic, or can make use of another detectable property. Detection can also be performed using the polymerase chain reaction (PCR) mechanism or a variant thereof. PCR is described in detail in U.S. Pat. No. 4,683,195 to Mullis et al. and U.S. Pat. No. 4,683,202 to Mullis et al. Other detection methods, including other amplification methods, are known in the art. One particularly suitable method uses reverse transcription with MMLV reverse transcriptase followed by PCR.

Another aspect of methods of use of 9-substituted guanine derivatives according to the present invention is a method of regulating calcium channel function in a mammal comprising and administering an effective amount of the 9-substituted guanine derivative of the present invention to the mammal. The 9-substituted guanine derivatives that are particularly useful for this method comprise the following: compounds of formula (V), in which n is an integer from 1 to 6; $R_1$ is H, COOH, or $COOW_1$, where $W_1$ is lower alkyl, amino, or lower alkylamino; $R_2$ is H or OH; $R_3$ is H or OH. Dysfunction of calcium channels has been implicated in a wide spectrum of human cardiovascular (e.g., hypertension, arrythmia), respiratory (e.g., asthma), and neurological diseases (e.g., stroke, amyotrophic lateral sclerosis (ALS or Lou Gehrig's Disease), Alzheimer's disease and migraine). Therefore, regulation of calcium channel function is important. The effect of these compounds on calcium channel function can be determined by methods generally known in the art, such as blocking all but one class of the calcium channels with specific binding reagents and then determining the activity of the one remaining class of calcium channels.

Yet another aspect of a method of use of the present invention is a method of use of the 9-substituted guanine derivatives according to the present invention in reducing serum cholesterol. The method comprises a step of administering an effective amount of the 9-substituted guanine derivative of the present invention to the mammal. The 9-substituted guanine derivatives according to the present invention that are particularly useful for this method comprise compounds of formula (I), in which n is an integer from 1 to 6; $R_1$ is H, COOH, or $COOW_1$, where $W_1$ is lower alkyl, amino, or lower alkylamino; and $R_2$ is H or OH. The amount that is an effective amount can be determined from an assay of cholesterol levels in serum. Methods for the determination of serum cholesterol are well known in the art, and typically involve enzymatic reactions, beginning with the hydrolysis of cholesteryl esters to produce free cholesterol and then the oxidation of cholesterol with cholesterol oxidase to yield cholest-4-ene-3-one and hydrogen peroxide. Various methods can then be used to detect either the molecular oxygen consumed or the hydrogen peroxide produced. Such methods are described, for example, in N. W. Tietz, ed., "Clinical Chemistry" (W. B. Saunders Co., Philadelphia, 1986), pp. 882–886, incorporated herein by this reference.

Yet another aspect of the present invention is a method for increasing the level of HDL cholesterol in the blood serum of a mammal comprising the step of administering a 9-substituted guanine derivative according to the present invention to the mammal. The 9-substituted guanine derivatives according to the present invention that are particularly suitable for this method comprise compounds of formula (I), in which n is an integer from 1 to 6; $R_1$ is H, COOH, or $COOW_1$, where $W_1$ is lower alkyl, amino, or lower alkylamino; and $R_2$ is H or OH. The amount that is an effective amount can be determined from the assay of HDL cholesterol levels in serum. HDL cholesterol can be determined by selective precipitation of VLDL and LDL cholesterol with various polyanions, e.g., heparin and manganese chloride, followed by measurement of the cholesterol concentration in the supernatant containing the HDL. Other methods are also known in the art.

IV. METHODS OF SYNTHESIS OF COMPOUNDS OF THE PRESENT INVENTION

Methods for synthesis of compounds according to the present invention are modified from those described, for example, in U.S. Pat. No. 5,091,432 to Glasky, incorporated herein by this reference. In one general route, the purine moiety containing the guanine residue is substituted with a linker which in turn is linked to the second pharmacophore that comprises the molecule. This route comprises the steps of:

(1) synthesis of an appropriately substituted purine moiety linked to an aliphatic linker in which the linker is terminated with a carboxyl group protected such as with an alkyl ester;

(2) hydrolyzing the alkyl ester (or other analogous protecting group) to yield a carboxylic acid;

(3) activating the free carboxylic acid by converting it to a nitrophenyl ester;

(4) reacting the nitrophenyl ester with an appropriate group that can form an amide or other stable covalent linkage with the carboxyl moiety, with appropriate protection for the moiety reacting with the ester if required; and (5) hydrolyzing the protective group protecting the moiety reacting with the ester to produce the final product.

The length of the aliphatic linker covalently bound to the purine moiety can be varied to vary the distance between the guanine moiety and the other biologically active group in the compound of the present invention.

Alternatively, the purine ring can be formed in stages, with the attachment of the linker and the second pharmacophore occurring before the closure of the purine ring. This route involves:

(1) the formation of aminocyanacetamide;

(2) the reaction of aminocyanacetamide with triethyl orthoformate and acetonitrile to form an amido ester derivative of aminocyanacetamide;

(3) the formation of a compound having a reactive amino group on a hydrocarbyl moiety, the hydrocarbyl moiety being linked to an amide group to a derivative of a physiologically active moiety, the derivative being protected, such as with an ester group;

(4) the reaction of the amido ester with the compound having the reactive amino group on the hydrocarbyl moiety;

(5) formation of the 6-membered heterocyclic ring of the guanine moiety; and (6) hydrolysis of the protecting group, if present, to form the final product.

The step of the formation of the 6-membered heterocyclic ring of the guanine moiety can be performed either by the ring closure of Yamazaki (A. Yamazaki et al., "Synthesis of Guanosine and Its Derivatives from 5-Amino-1-β-D-Ribofuranosyl-4-Imidazolecarboxamide I. Ring Closure with Benzoyl Isothiocyanate, *J. Org. Chem.* 32:1825–1828 (1967) or, alternatively, by the method of Clausen (B. Alhede et al., "A Simple and Efficient Synthesis of 9-Substituted Guanines. Cyclodesulfurization of 1-Substituted 5-[(Thiocarbamoyl)amino]imidazole-4-carboxamides under Aqueous Basic Conditions," *J. Org. Chem.* 56:2139–2143 (1991)) involving catalysis by a heavy metal salt such as $Cu^{2+}$, $Ag^+$, or $Hg^{2+}$ in aqueous NaOH, or, alternatively, by S-oxidation with hydrogen peroxide or sodium perborate in aqueous sodium hydroxide. This method was demonstrated for guanine moieties substituted with various substituents at the nitrogen at the 9-position of the guanine moiety.

Other synthetic routes are known in the art.

ADVANTAGES OF THE INVENTION

The present invention provides 9-substituted guanine derivatives that exert a number of biological and physiological functions. The 9-substituted guanine derivatives of the present invention are capable of passing through the blood-brain barrier and exerting their effects in the central nervous system. These compounds are capable of exerting a number of effects, including the stimulation of nerve growth regeneration, regulating calcium channel function, reducing total serum cholesterol, and increasing HDL cholesterol. The molecule linked to the guanine moiety and the length of the linker can be chosen to optimize the desired activity or range of activities of the molecule.

Although the present invention has been described in considerable detail, with reference to certain preferred versions thereof, other versions and embodiments are possible. Therefore, the scope of the invention is determined by the following claims.

We claim:

1. A 9-substituted guanine compound of formula (II)

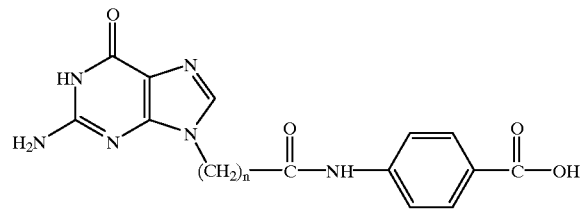

(II)

wherein n is an integer from 1 to 6.

2. The 9-substituted guanine compound of claim 1 wherein n is 2 and the compound is N-4-carboxyphenyl-3-(2-amino-6-oxohydropurin-9-yl) propanamide.

3. A pharmaceutical composition comprising:
   (a) an effective amount of the 9-substituted guanine compound of claim 1; and
   (b) a pharmaceutically acceptable carrier.

4. The pharmaceutical composition of claim 3 wherein the 9-substituted guanine compound is N-(4-carboxyphenyl)-3-(2-amino-6-oxohydropurin-9-yl) propanamide.

5. A 9-substituted guanine compound of formula (III)

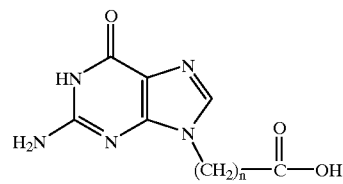

(III)

wherein n is an integer with a value of 1, 5, or 6.

6. A pharmaceutical composition comprising:
   (a) an effective amount of a 9-substituted guanine compound of formula (III) wherein n is an integer from 1 to 6; and
   (b) a pharmaceutically acceptable carrier.

7. The pharmaceutical composition of claim 6 wherein the 9-substituted guanine compound is 3-(2-amino-6-oxohydropurin-9-yl) propanoic acid.

8. A 9-substituted guanine compound of formula (IV)

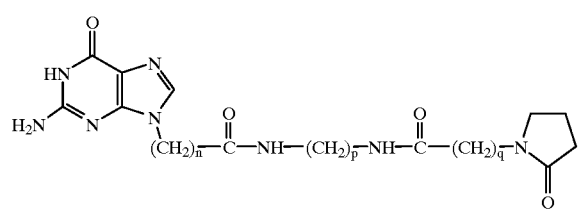

(IV)

wherein n is an integer from 1 to 6, p is an integer from 1 to 6, and q is an integer from 1 to 3.

9. The 9-substituted guanine compound of claim 8 wherein n is 2, p is 2, q is 1, and the compound is N-[2-[[2-(2-oxopyrrolidin-1-yl)-1-oxoethyl]amino]ethyl] propanamide.

10. A pharmaceutical composition comprising:
(a) an effective amount of the 9-substituted guanine compound of claim 8; and
(b) a pharmaceutically acceptable carrier.

11. The pharmaceutical composition of claim 10 wherein the 9-substituted guanine compound is N-[2-[[2-(2-oxopyrrolidin-1-yl)-1-oxoethyl]amino]ethyl] propanamide.

12. A 9-substituted guanine compound of formula (V)

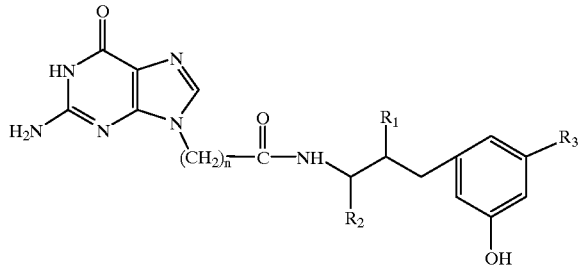

wherein n is an integer from 1 to 6, $R_1$ is selected from the group consisting of H, COOH, and $COOW_1$, where $W_1$ is selected from the group consisting of lower alkyl, amino, and lower alkylamino, $R_2$ is selected from the group consisting of H and OH, and $R_3$ is selected from the group consisting of H and OH.

13. The 9-substituted guanine compound of claim 12 wherein n is 2.

14. The 9-substituted guanine compound of claim 13 wherein the compound is N-(2-(3,4-dihydroxyphenyl)ethyl-3-(2-amino-6-oxohydropurin-9-yl) propanamide, where $R_1$ is H, $R_2$ is H, and $R_3$ is OH.

15. The 9-substituted guanine compound of claim 13 wherein the compound is N-(2-hydroxy-2-(3,4-dihydroxyphenyl)ethyl-3-(2-amino-6-oxohydropurin-9-yl) propanamide, where $R_1$ is H, $R_2$ is OH, and $R_3$ is OH.

16. The 9-substituted guanine compound of claim 13 wherein the compound is N-(1-carboxyl-2-(3,4-dihydroxyphenyl)ethyl-3-(2-amino-6-oxohydropurin-9-yl) propanamide, where $R_1$ is COOH, $R_2$ is H, and $R_3$ is H.

17. A pharmaceutical composition comprising:
(a) an effective amount of the 9-substituted guanine compound of claim 12; and
(b) a pharmaceutically acceptable carrier.

18. The pharmaceutical composition of claim 17 wherein the 9-substituted guanine compound is the compound of formula (V) wherein n is 2.

19. The pharmaceutical composition of claim 18 wherein the 9-substituted guanine compound is N-(2-(3,4-dihydroxyphenyl)ethyl-3-(2-amino-6-oxohydropurin-9-yl) propanamide.

20. The pharmaceutical composition of claim 18 wherein the 9-substituted guanine compound is N-(2-hydroxy-2-(3,4-dihydroxyphenyl)ethyl-3-(2-amino-6-oxohydropurin-9-yl) propanamide.

21. The pharmaceutical composition of claim 18 wherein the 9-substituted guanine compound is N-(1-carboxyl-2-(3,4-dihydroxyphenyl)ethyl-3-2-amino-6-oxohydropurin-9-yl) propanamide.

22. A method of treating a disease or a condition in a mammal treatable by inhibiting the activity of a monoamine oxidase comprising the step of administering an effective amount of the 9-substituted guanine compound of claim 12 to the mammal.

23. The method of claim 22 wherein the 9-substituted guanine compound is the compound of formula (V) wherein n is 2.

24. The method of claim 23 wherein the 9-substituted guanine compound is N-(2-(3,4-dihydroxyphenyl)ethyl-3-(2-amino-6-oxohydropurin-9-yl) propanamide.

25. The method of claim 23 wherein the 9-substituted guanine compound is N-(2-hydroxy)-2-(3,4-dihydroxyphenyl)ethyl-3-(2-amino-6-oxohydropurin-9-yl) propanamide.

26. The method of claim 23 wherein the 9-substituted guanine compound is N-(1-carboxyl)-2-(3,4-dihydroxyphenyl) ethyl-3-(2-amino-6-oxohydropurin-9-yl) propanamide.

27. A method of regulating calcium channel function in a mammal comprising administering an effective amount of the 9-substituted guanine compound of claim 22 to the mammal.

28. The method of claim 27 wherein the 9-substituted guanine compound is the compound of formula (V) wherein n is 2.

29. The method of claim 25 wherein the 9-substituted guanine compound is N-(2-(3,4-dihydroxyphenyl)ethyl-3-(2-amino-6-oxohydropurin-9-yl) propanamide.

30. The method of claim 29 wherein the 9-substituted guanine compound is N-(2-hydroxy)-2-(3,4-dihydroxyphenyl) ethyl-3-(2-amino-6-oxohydropurin-9-yl) propanamide.

31. The method of claim 29 wherein the 9-substituted guanine compound is N-(1-carboxyl)-2-(3,4-dihydroxyphenyl) ethyl-3-(2-amino-6-oxohydropurin-9-yl propanamide.

32. A 9-substituted guanine compound of formula (VI)

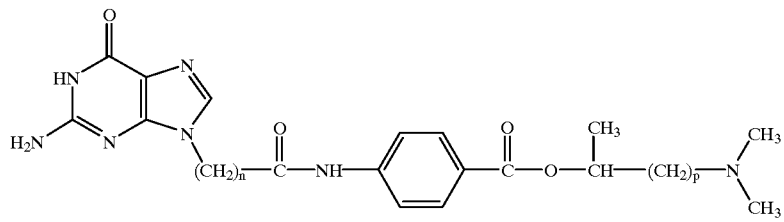

wherein n is an integer from 1 to 6 and p is an integer from 1 to 3.

33. The 9-substituted guanine compound of claim 32 wherein n is 2, p is 1, and the compound is the 1-(dimethylamino)-2-propyl ester of N-4-carboxyphenyl-3-(2-amino-6-oxohydropurin-9-yl) propanamide.

34. A pharmaceutical composition comprising:
(a) an effective amount of the 9-substituted guanine compound of claim 32; and
(b) a pharmaceutically acceptable carrier.

35. The pharmaceutical composition of claim 34 wherein the 9-substituted guanine compound is the 1-(dimethylamino)-2-propyl ester of N-4-carboxyphenyl-3-(2-amino-6-oxohydropurin-9-yl) propanamide.

36. A 9-substituted guanine compound of formula (VII)

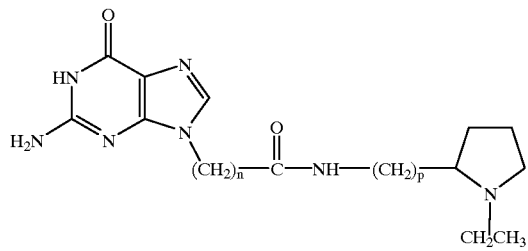

(VII)

wherein n is an integer from 1 to 6 and p is an integer from 1 to 3.

37. The 9-substituted guanine compound of claim 36 wherein n is 2, p is 1, and the compound is N-(1-ethylpyrrolidin-2-yl)methyl-3-(2-amino-6-oxohydropurin-9-yl) propanamide.

38. A 9-substituted guanine compound of formula (VIII)

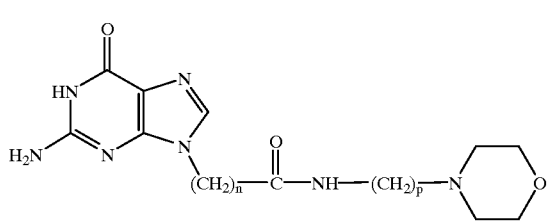

(VIII)

wherein n is an integer from 1 to 6 and p is an integer from 1 to 6.

39. The 9-substituted guanine compound of claim 38 wherein n is 2, p is 2, and the compound is N-[2-(4-morpholinyl)ethyl]-3-(2-amino-6-oxohydropurin-9-yl) propanamide.

40. The 9-substituted guanine compound of claim 38 wherein n is 2, p is 3, and the compound is N-[3-(4-morpholinyl)propyl]-3-(2-amino-6-oxohydropurin-9-yl) propanamide.

41. A 9-substituted guanine compound of formula (IX)

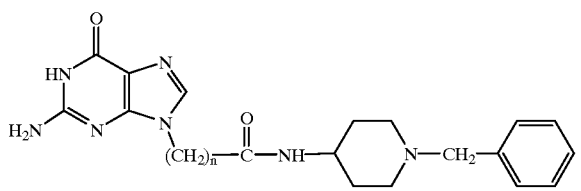

(IX)

wherein n is an integer from 1 to 6.

42. The 9-substituted guanine compound of claim 41 wherein n is 2 and the compound is N-(1-benzylpiperidin-4-yl)-3-(2-amino-6-oxohydropurin-9-yl) propanamide.

43. A 9-substituted guanine compound of formula (X)

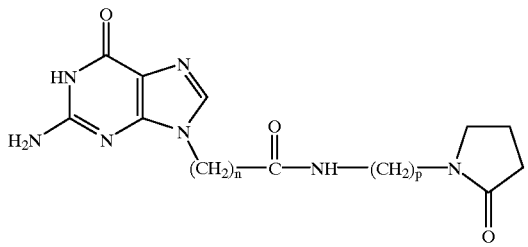

(X)

wherein n is an integer from 1 to 6 and p is an integer from 1 to 6.

44. The 9-substituted guanine compound of claim 43 wherein n is 2, p is 3, and the compound is N-[3-(2-oxopyrrolidin-1-yl)propyl]-3-(2-amino-6-oxohydropurin-9-yl) propanamide.

45. A 9-substituted guanine compound of formula (XI)

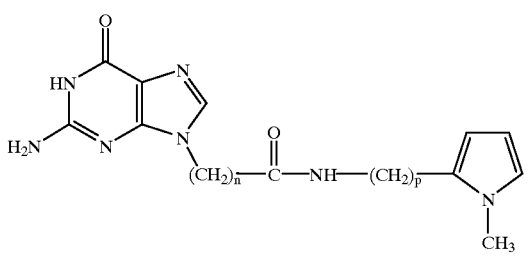

(XI)

wherein n is an integer from 1 to 6 and p is an integer from 1 to 3.

46. The 9-substituted guanine compound of claim 45 wherein n is 2, p is 2, and the compound is N-[2-(1-methylpyrrol-2-yl)ethyl]-3-(2-amino-6-oxohydropurin-9-yl) propanamide.

47. A 9-substituted guanine compound of formula (XII)

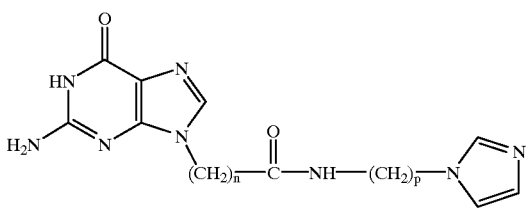

(XII)

wherein n is an integer from 1 to 6 and p is an integer from 1 to 6.

48. The 97substituted guanine compound of claim 47 wherein n is 2, p is 3, and the compound is N-[3-(1-imidazolyl)propyl]-3-(2-amino-6-oxohydropurin-9-yl) propanamide.

49. A 9-substituted guanine compound of formula (XIII)

(XIII)

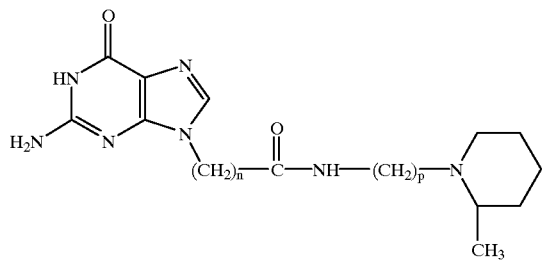

wherein n is an integer from 1 to 6 and p is an integer from 1 to 6.

50. The 9-substituted guanine compound of claim 49 wherein n is 2, p is 3, and the compound is N-[3-(2-methylpiperidin-1-yl)propyl]-3-(2-amino-6-oxohydropurin-9-yl) propanamide.

51. A 9-substituted guanine compound of formula (XIV)

(XIV)

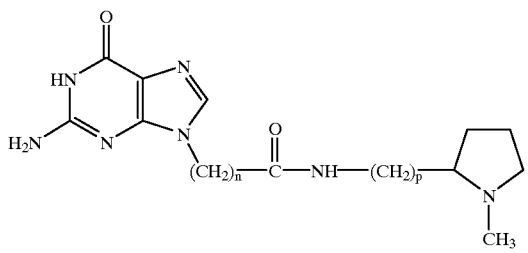

wherein n is an integer from 1 to 6 and p is an integer from 1 to 6.

52. The 9-substituted guanine compound of claim 51 wherein n is 2, p is 2, and the compound is N-[2-(1-methylpyrrolidin-2-yl)ethyl]-3-(2-amino-6-oxohydropurin-9-yl) propanamide.

53. A 9-substituted guanine compound of formula (XV)

(XV)

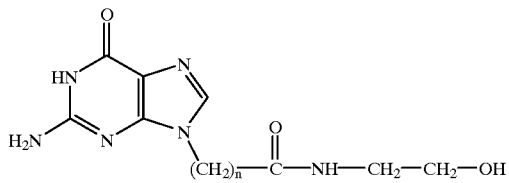

wherein n is an integer from 1 to 6.

54. The 9-substituted guanine compound of claim 53 wherein n is 2 and the compound is N-(2-hydroxyethyl)-3-(2-amino-6-oxohydropurin-9-yl) propanamide.

55. A 9-substituted guanine compound of formula (XVI)

(XVI)

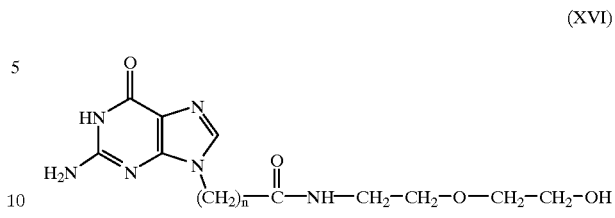

wherein n is an integer from 1 to 6.

56. The 9-substituted guanine compound of claim 55 wherein n is 2 and the compound is N-[2-(2-hydroxyethoxy)ethyl]-3-(2-amino-6-oxohydropurin-9-yl) propanamide.

57. A 9-substituted guanine compound of formula (XVII)

(XVII)

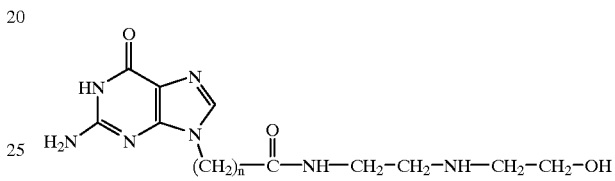

wherein n is an integer from 1 to 6.

58. The 9-substituted guanine compound of claim 57 wherein n is 2 and the compound is N-[2-[(2-hydroxyethyl)amino]ethyl]-3-(2-amino-6-oxohydropurin-9-yl) propanamide.

59. A 9-substituted guanine compound of formula (XVIII)

(XVIII)

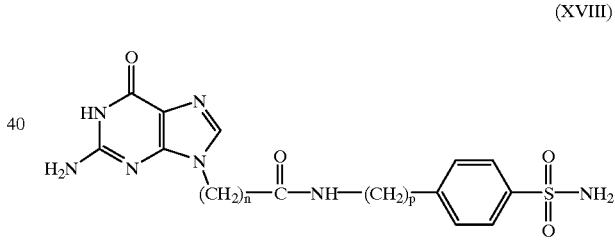

wherein n is an integer from 1 to 6 and p is an integer from 1 to 6.

60. The 9-substituted guanine compound of claim 59 wherein n is 2, p is 2, and the compound is N-[2-(4-aminosulfonylphenyl)ethyl]-3-(2-amino-6-oxohydropurin-9-yl) propanamide.

61. A 9-substituted guanine compound of formula (XIX)

(XIX)

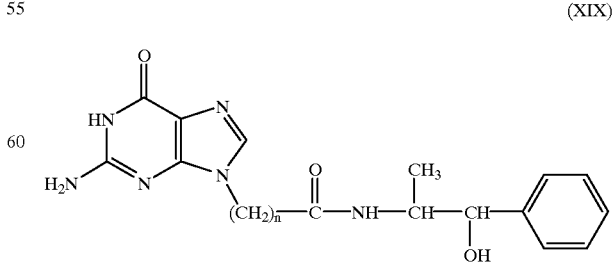

wherein n is an integer from 1 to 6.

62. The 9-substituted guanine compound of claim 61 wherein n is 2 and the compound is N-[(2-hydroxy-1-methyl-2-phenyl)ethyl]-3-(2-amino-6-oxohydropurin-9-yl)propanamide.

63. A 9-substituted guanine compound of formula (XX)

(XX)

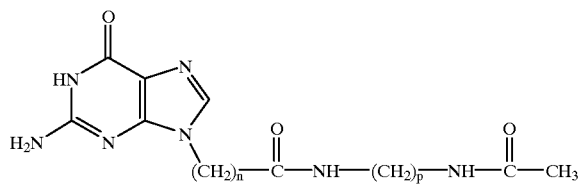

wherein n is an integer from 1 to 6 and p is an integer from 1 to 6.

64. The 9-substituted guanine compound of claim 63 wherein n is 2, p is 2, and the compound is N-[2-[(1-oxoethyl)amino]ethyl]-3-(2-amino-6-oxohydropurin-9-yl)propanamide.

65. A 9-substituted guanine compound of formula (XXI)

(XXI)

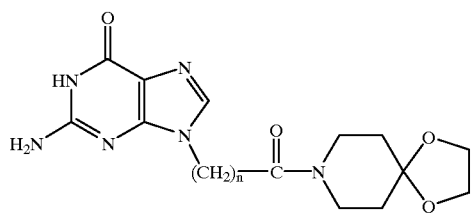

wherein n is an integer from 1 to 6.

66. The 9-substituted guanine compound of claim 65 wherein n is 2 and the compound is 1-[1,4-dioxa-8-azaspiro[4.5]dec-8-yl]-3-(2-amino-6-oxohydropurin-9-yl)propanone.

67. A 9-substituted guanine compound of formula (XXII)

(XXII)

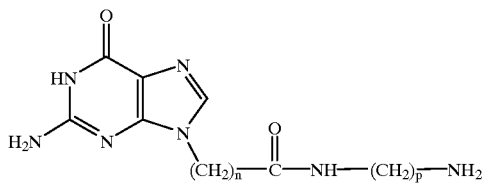

wherein n is an integer from 1 to 6 and p is an integer from 1 to 6.

68. The 9-substituted guanine compound of claim 67 wherein n is 2, p is 2, and the compound is N-(2-aminoethyl)-3-(2-amino-6-oxohydropurin-9-yl)propanamide.

69. The 9-substituted guanine compound of claim 67 wherein n is 2, p is 3, and the compound is N-(3-aminopropyl)-3-(2-amino-6-oxohydropurin-9-yl)propanamide.

70. A 9-substituted guanine compound of formula (XXIII)

(XXIII)

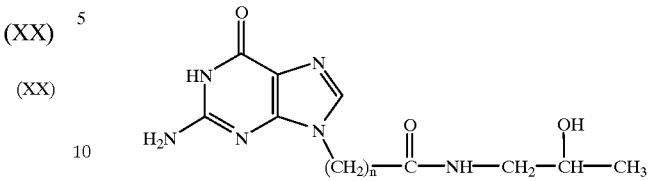

wherein n is an integer from 1 to 6.

71. The 9-substituted guanine compound of claim 70 wherein n is 2 and the compound is N-(2-hydroxypropyl)-3-(2-amino-6-oxohydropurin-9-yl)propanamide.

72. A 9-substituted guanine compound of formula (XXIV)

(XXIV)

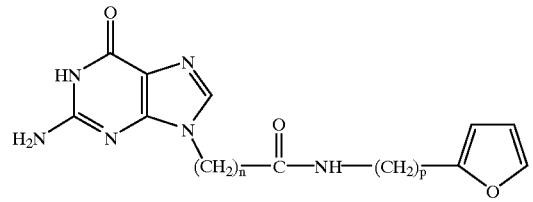

wherein n is an integer from 1 to 6 and p is an integer from 1 to 3.

73. The 9-substituted guanine compound of claim 72 wherein n is 2, p is 1, and the compound is N-[(2-furanyl)methyl]-3-(2-amino-6-oxohydropurin-9-yl)propanamide.

74. A 9-substituted guanine compound of formula (XXV)

(XXV)

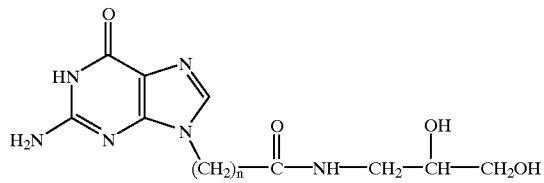

wherein n is an integer from 1 to 6.

75. The 9-substituted guanine compound of claim 74 wherein n is 2 and the compound is N-(2,3-dihydroxyprop-1-yl)-3-(2-amino-6-oxohydropurin-9-yl)propanamide.

76. A 9-substituted guanine compound of formula (XXVI)

(XXVI)

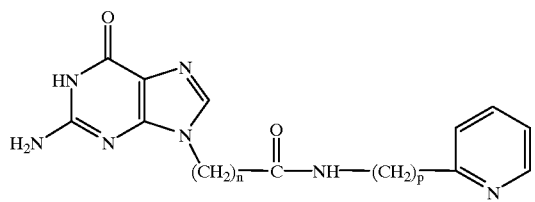

wherein n is an integer from 1 to 6 and p is an integer from 1 to 3.

77. The 9-substituted guanine compound of claim 76 wherein n is 2, p is 1, and the compound is N-[(2-pyridinyl)methyl]-3-(2-amino-6-oxohydropurin-9-yl)propanamide.

78. A 9-substituted guanine compound of formula (XXVII)

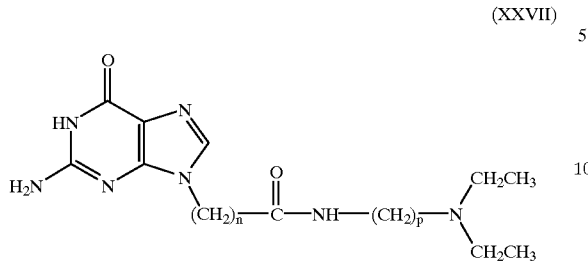

wherein n is an integer from 1 to 6 and p is an integer from 2 to 6.

79. The 9-substituted guanine compound of claim 78 wherein n is 2, p is 2, and the compound is N-[(2-diethylamino)ethyl]-3-(2-amino-6-oxohydropurin-9-yl)propanamide.

80. A 9-substituted guanine compound of formula (XXVIII)

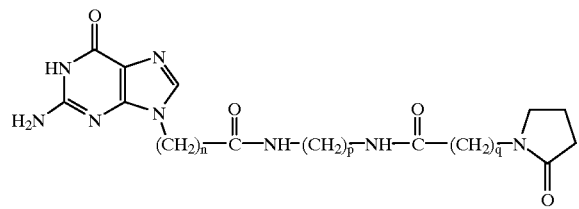

where n is an integer from 1 to 6, p is an integer from 1 to 6, and q is an integer from 1 to 3.

81. The 9-substituted guanine compound of claim 80 wherein n is 2, p is 2, q is 1, and the compound is N-[2-[[2-(2-oxopyrrolidin-1-yl)-1-oxoethyl]amino]ethyl]-3-(2-amino-6-oxohydropurin-9-yl)propanamide.

82. A 9-substituted guanine compound of formula (XXIX)

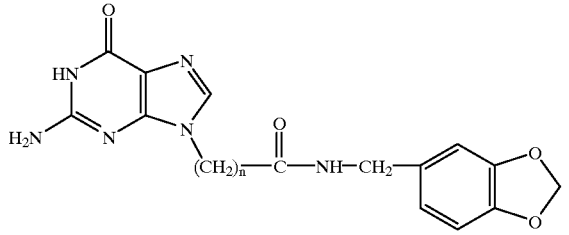

wherein n is an integer from 1 to 6.

83. The 9-substituted guanine compound of claim 82 wherein n is 2 and the compound is N-piperonyl-3-(2-amino-6-oxohydropurin-9-yl)propanamide.

84. A 9-substituted guanine compound of formula (XXX)

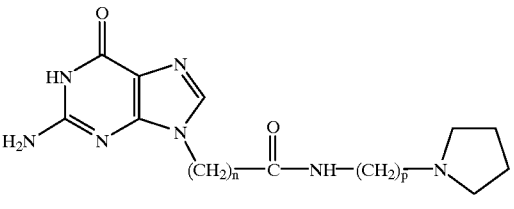

wherein n is an integer from 1 to 6 and p is an integer from 1 to 6.

85. The 9-substituted guanine compound of claim 84 wherein n is 2, p is 2, and the compound is N-[(1-pyrrolidinyl)ethyl]-3-(2-amino-6-oxohydropurin-9-yl)propanamide.

86. A 9-substituted guanine compound of formula (XXXI)

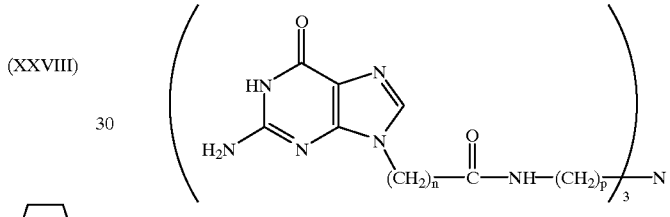

wherein n is an integer from 1 to 6 and p is an integer from 1 to 6.

87. The 9-substituted guanine compound of claim 86 wherein n is 2, p is 2, and the compound is N, N', N'',-tri[2-[3-(2-amino-6-oxohydropurin-9-yl)-1-oxopropyl]aminoethyl]amine.

88. A 9-substituted guanine compound of formula (XXXII)

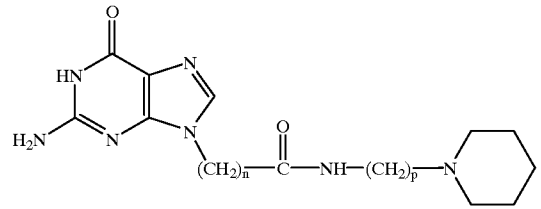

wherein n is an integer from 1 to 6 and p is an integer from 1 to 6.

89. The 9-substituted guanine compound of claim 88 wherein n is 2, p is 2, and the compound is N-[[2-(1-piperidinyl)]ethyl]-3-(2-amino-6-oxohydropurin-9-yl)propanamide.

90. A 9-substituted guanine compound of formula (XXXIII)

(XXXIII)

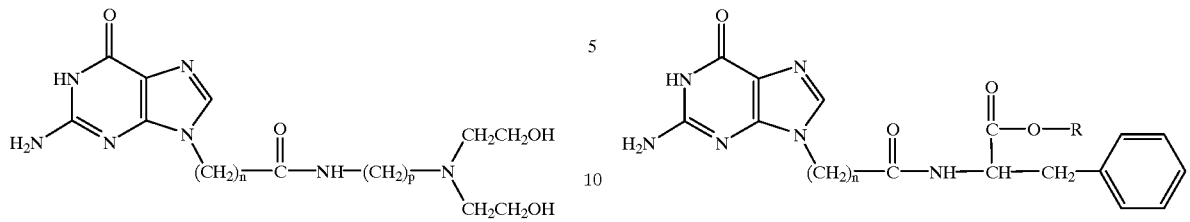

wherein n is an integer from 1 to 6 and p is an integer from 2 to 6.

91. The 9-substituted guanine compound of claim 90 wherein n is 2, p is 2, and the compound is N-[2-(2,2'-diethanolamino)ethyl]-3-(2-amino-6-oxohydropurin-9-yl)propanamide.

92. A 9-substituted guanine compound of formula (XXXIV)

(XXXIV)

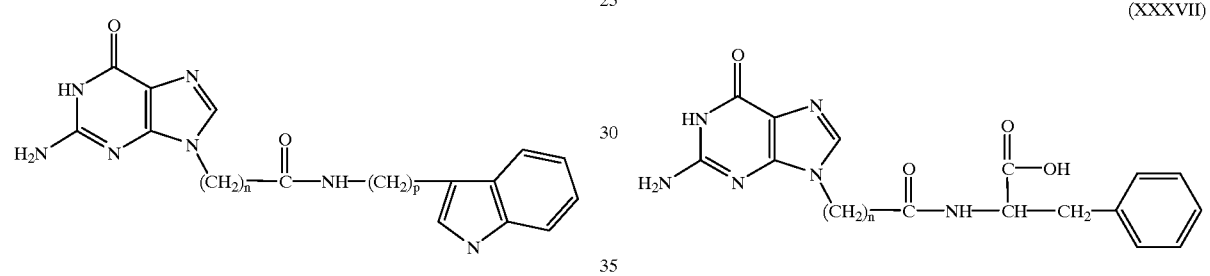

wherein n is an integer from 1 to 6 and p is an integer from 1 to 6.

93. The 9-substituted guanine compound of claim 92 wherein n is 2, p is 2, and the compound is N-[2-(1H-indol-3-yl)ethyl]-3-(2-amino-6-oxohydropurin-9-yl)propanamide.

94. A 9-substituted guanine compound of formula (XXXV)

(XXXV)

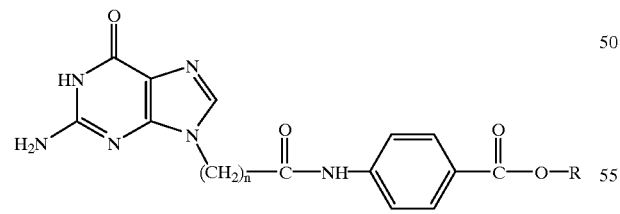

wherein n is an integer from 1 to 6 and R is a lower alkyl residue of $C_1$ to $C_6$.

95. The 9-substituted guanine compound of claim 94 wherein n is 2, R is ethyl, and the compound is N-(4-carboethoxyphenyl)-3-(2-amino-6-oxohydropurin-9-yl)propanamide.

96. A 9-substituted guanine compound of formula (XXXVI)

(XXXVI)

wherein n is an integer from 1 to 6 and R is a lower alkyl residue of $C_1$ to $C_6$.

97. The 9-substituted guanine compound of claim 96 wherein n is 2, R is ethyl, and the compound is N-(1-carboethoxy-2-phenyl)-3-(2-amino-6-oxohydropurin-9-yl)propanamide.

98. A 9-substituted guanine compound of formula (XXXVII)

(XXXVII)

wherein n is an integer from 1 to 6.

99. The 9-substituted guanine compound of claim 98 wherein n is 2 and the compound is N-[(1-carboxy-2-phenyl)ethyl]-3-(2-amino-6-oxohydropurin-9-yl)propanamide.

100. A 9-substituted guanine compound of formula (XXXVIII)

(XXXVIII)

wherein n is an integer from 1 to 6.

101. The 9-substituted guanine compound of claim 100 wherein n is 2 and the compound is N-[2-(2-deoxy-glucopyranosyl)]-3-(2-amino-6-oxohydropurin-9-yl)propanamide.

102. A 9-substituted guanine compound of formula (XXXIX)

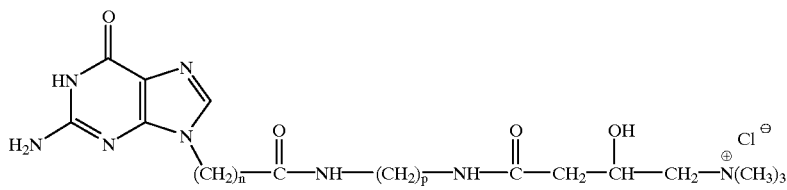

(XXXIX)

wherein n is an integer from 1 to 6 and p is an integer from 1 to 6.

103. The 9-substituted guanine compound of claim 102 wherein n is 2, p is 2, and the compound is 4-[[2-[[3-(2-amino-6-oxohydropurin-9-yl)]-1-oxopropyl]amino]ethyl]amino]-2-hydroxy-4-oxo-N,N,N-trimethyl-1-butanaminium chloride.

104. A 9-substituted guanine compound of formula (XL)

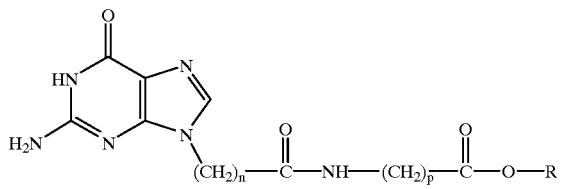

(XL)

wherein n is an integer from 1 to 6, p is an integer from 2 to 6, and R is a lower alkyl residue of $C_1$ to $C_6$.

105. The 9-substituted guanine compound of claim 104 wherein n is 2, p is 3, R is ethyl, and the compound is N-[(3-carboethoxy)propyl]-3-(2-amino-6-oxohydropurin-9-yl)propanamide.

106. A 9-substituted guanine compound of formula (XLI)

(XLI)

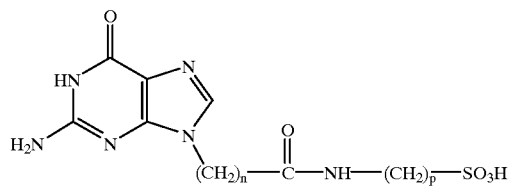

wherein n is an integer from 1 to 6 and p is an integer from 1 to 3.

107. The 9-substituted guanine compound of claim 106 wherein n is 2, p is 3, and the compound is N-[(3-sulfo)propyl]-3-(2-amino-6-oxohydropurin-9-yl)propanamide.

108. A 9-substituted guanine compound of formula (XLII)

(XLII)

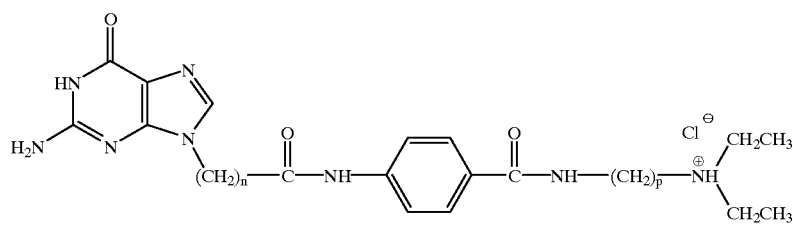

wherein n is an integer from 1 to 6 and p is an integer from 1 to 6.

109. The 9-substituted guanine compound of claim 108 wherein n is 2, p is 2, and the compound is 4-[[3-(2-amino-6-oxohydropurin-9-y)-1-oxopropyl]amino]-N-2-[(diethylamino)ethyl]benzamide hydrochloride.

110. A 9-substituted guanine compound of formula (XLIII)

(XLIII)

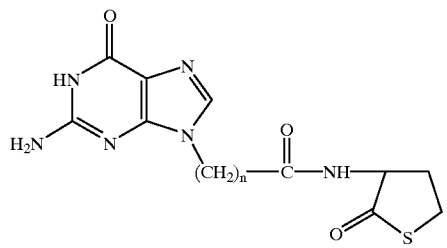

wherein n is an integer from 1 to 6.

111. The 9-substituted guanine compound of claim 110 wherein n is 2 and the compound is N-(2-oxothiolan-3-yl)-3-(2-amino-6-oxohydropurin-9-yl)propanamide.

112. A 9-substituted guanine compound of formula (XLIV)

(XLIV)

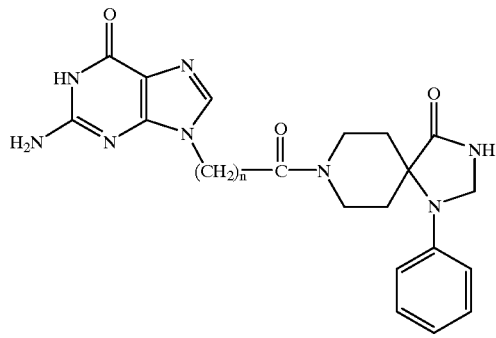

wherein n is an integer from 1 to 6.

113. The 9-substituted guanine compound of claim 112 wherein n is 2 and the compound is 3-(2-amino-6-oxohydropurin-9-yl)-1-(1-phenyl-4-oxo-1,3,8-triazaspiro[4.5]dec-8-yl)-propanone.

114. A 9-substituted guanine compound of formula (XLV)

(XLV)

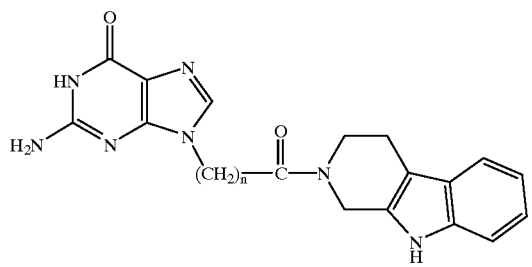

wherein n is an integer from 1 to 6.

115. The 9-substituted guanine compound of claim 114 wherein n is 2 and the compound is 3-(2-amino-6-oxohydropurin-9-yl)-1-(1,2,3,4-tetrahydro-2-azacarbazo-2-yl)propanone.

116. A 9-substituted guanine compound of formula (XLVI)

(XLVI)

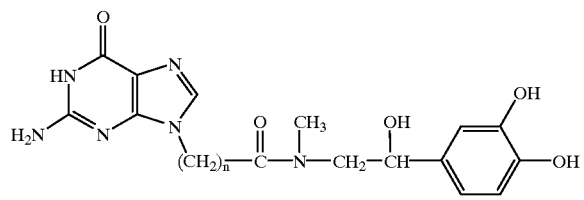

wherein n is an integer from 1 to 6.

117. The 9-substituted guanine compound of claim 116 wherein n is 2 and the compound is N-[2-(3,4-dihydroxyphenyl)-2-hydroxyethyl]-N-methyl-3-(2-amino-6-oxohydropurin-9-yl)propanamide.

118. A 9-substituted guanine compound of formula (XLVII)

(XLVII)

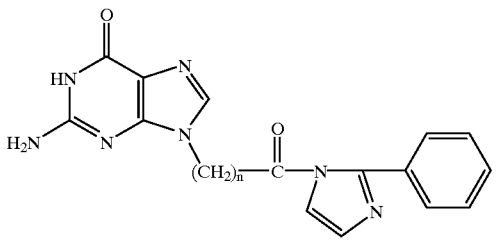

wherein n is an integer from 1 to 6.

119. The 9-substituted guanine compound of claim 118 wherein n is 2 and the compound is 3-(2-amino-6-oxohydropurin-9-yl)-1-(2-phenylimidazo-1-yl)propanone.

120. A 9-substituted guanine compound of formula (XLVIII)

(XLVIII)

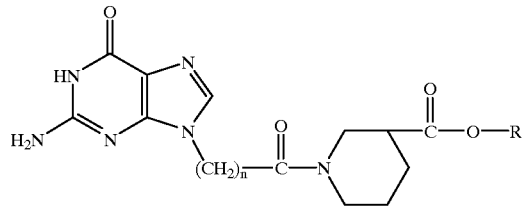

wherein n is an integer from 1 to 6 and R is a lower alkyl residue of $C_1$ to $C_6$.

121. The 9-substituted guanine compound of claim 120 wherein n is 2, R is ethyl, and the compound is ethyl 1-[3-(2-amino-6-oxohydropurin-9-yl)-1-oxopropyl]-3-piperidine carboxylate.

122. A 9-substituted guanine compound of formula (XLIX)

(XLIX)

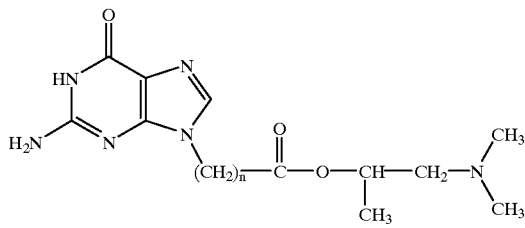

wherein n is an integer from 1 to 6.

123. The 9-substituted guanine derivative compound of claim 122 wherein n is 2 and the compound is N-[4-(1-dimethylamino-2-carbopropoxy)phenyl]-3-(2-amino-6-oxohydropurin-9-yl)propanamide.

* * * * *